United States Patent
Maleczka, Jr. et al.

(10) Patent No.: US 6,828,466 B2
(45) Date of Patent: Dec. 7, 2004

(54) PROCESS FOR THE SYNTHESIS OF PHENOLS FROM ARENES

(75) Inventors: Robert E. Maleczka, Jr., DeWitt, MI (US); Milton R. Smith, III, East Lansing, MI (US); Daniel Holmes, DeWitt, MI (US); Feng Shi, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 87 days.

(21) Appl. No.: 10/620,122

(22) Filed: Jul. 15, 2003

(65) Prior Publication Data

US 2004/0030197 A1 Feb. 12, 2004

Related U.S. Application Data

(60) Provisional application No. 60/397,366, filed on Jul. 19, 2002.

(51) Int. Cl.$^7$ ............................................ C07C 37/00
(52) U.S. Cl. .................. 568/803; 546/303; 560/65; 560/67; 564/442; 568/650; 568/651; 568/765; 568/774; 568/775; 568/800
(58) Field of Search ................. 568/774, 775, 568/651, 650, 765, 800, 803; 560/65, 67; 564/442; 546/303

(56) References Cited

U.S. PATENT DOCUMENTS 3,553,271 A * 1/1971 Crenne ...................... 568/629

* cited by examiner

Primary Examiner—Michael L. Shippen
(74) Attorney, Agent, or Firm—Ian C. McLeod

(57) ABSTRACT

A process to synthesize substituted phenols such as those of the general formula RR'R"Ar(OH) wherein R, R', and R" are each independently hydrogen or any group which does not interfere in the process for synthesizing the substituted phenol including, but not limited to, halo, alkyl, alkoxy, carboxylic ester, amine, amide; and Ar is any variety of aryl or hetroaryl by means of oxidation of substituted arylboronic esters is described. In particular, a metal-catalyzed C—H activation/borylation reaction is described, which when followed by direct oxidation in a single or separate reaction vessel affords phenols without the need for any intermediate manipulations. More particularly, a process wherein Ir-catalyzed borylation of arenes using pinacolborane (HBPin) followed by oxidation of the intermediate arylboronic ester by OXONE is described.

24 Claims, 2 Drawing Sheets

34    35    36

37    38    39

40    41    42

43    44    45

PROCESS FOR THE SYNTHESIS OF PHENOLS FROM ARENES

CROSS-REFERENCE TO RELATED APPLICATION

Figure 1:
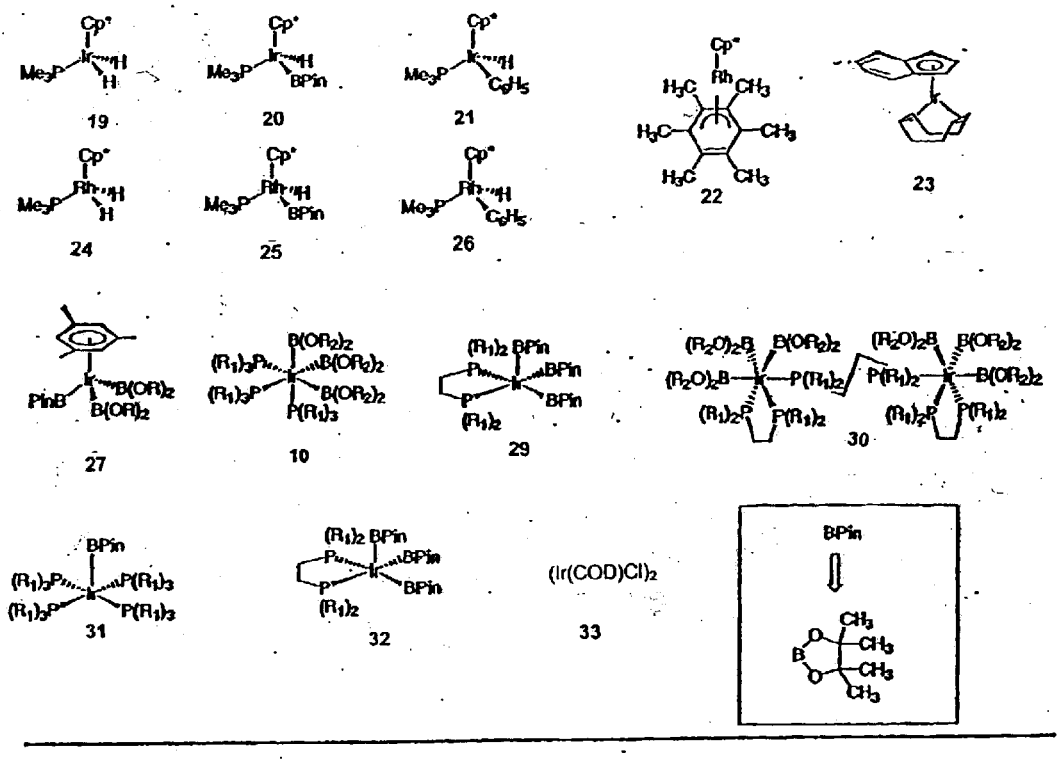
Figure 1:
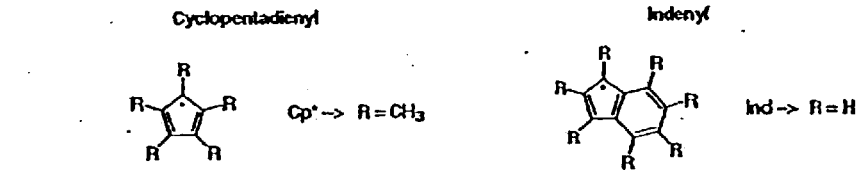

This application claims priority to U.S. Provisional Patent Application No. 60/397,366 which was filed Jul. 19, 2002.

STATEMENT REGARDING FEDERALLY SPONSORED RESEARCH OR DEVELOPMENT

This invention was supported in part by National Institutes of Health, National Institute of General Medical Sciences Grant No. GM63188 and National Science Foundation Grant No. CHE-9984644. The U.S. government has certain rights in this invention.

REFERENCE TO A "COMPUTER LISTING APPENDIX SUBMITTED ON A COMPACT DISC"

Not Applicable.

BACKGROUND OF THE INVENTION

(1) Field of the Invention

The present invention relates to a process for synthesizing various substituted phenols such as those of the general formula RR'R"Ar(OH) wherein R, R', and R" are each independently hydrogen or any group which does not interfere in the process for synthesizing the substituted phenol including, but not limited to, halo, alkyl, alkoxy, carboxylic ester, amine, amide; and Ar is any variety of aryl or hetroaryl by oxidation of substituted arylboronic esters. In particular, the present invention relates to a metal-catalyzed C—H activation/borylation reaction, which when followed by direct oxidation in the same or separate reaction vessel affords phenols without the need for any intermediate manipulations. More particularly, the present invention relates to the Ir-catalyzed borylation of arenes using pinacolborane (HBPin) followed by oxidation of the intermediate arylboronic ester by OXONE to produce the substituted phenols.

(2) Description of Related Art

Phenols serve as synthetic building blocks for construction of compounds ranging from polymers to pharmaceuticals (Tyman, Synthetic and Natural Phenols; Elsevier: New York, (1996). Despite numerous phenol syntheses (Hanson et al., J. Chem. Soc., Perkin Trans 2: 1135–1150 (2002); George et al., J. Chem. Soc., Perkin Trans 1: 2529–2574 (2000); Sweeney, Contemp. Org. Synth. 4: 435–453 (1997) ;For more recent innovative approaches see: Hoarau and Pettus, Synlett 127–137 (2003); Guo et al., Org. Lett. 3: 1177–1180 (2001); Marchueta et al., Org. Lett. 3: 3197–3200 (2001); Serra et al., J. Org. Chem. 66: 7883–7888 (2001); Hashmi et al., J. Am. Chem. Soc. 122: 11553–11554 (2000); Gevorgyan and Yamamoto, J. Organomet. Chem. 576: 232–247 (1999)), straightforward routes to 3,5-disubstituted phenols bearing ortho/para-directing groups are lacking (For an alternative approach, see Keil et al., Ger. Offen. DE2344925 (1975)).

Traditional approaches to such phenols are obstructed by the fact that electronic effects typically govern regioselectivities in aromatic substitution chemistry. Thus, the 5-position in 1,3-disubstituted benzenes is notoriously inert when the substituents are ortho/para directors. Illustrative of this problem is 3-bromo-5-chlorophenol (1). To the best of our knowledge, the only two descriptions of this potentially useful (Höger et al., J. Am. Chem. Soc. 123: 5651–5659 (2001)) and versatile molecule dates back to 1926 (Hodgson and Wignall, J. Chem. Soc. 2077–2079 (1926); Kohn and Zandman, Monatsh. Chem. 47: 357–377 (1926)), including a synthesis by Hodgson and Wignall that requires ten steps starting from TNT!

Other methods for the synthesis of phenols, include electrophilic hydroxylation of aromatics, oxidation of aryl organometallic compounds, hydrolysis of aryl halides, hydrolysis of diazonium salts, and reduction of quinones. Of these, the hydrolysis of diazonium salts by aqueous acids or in the presence of cuprous oxide (see, for example: Cohen et al., J. Org. Chem. 42: 2053 (1977)) is an often used method and serves as a representative example of a previous approach.

While the hydrolysis of the diazonium salt can be high yielding, the salts themselves are often explosive and can be hard to manipulate. Furthermore, producing the above salts involves multiple steps. The diazonium salts are synthesized from the corresponding anilines by reaction with nitrous acid (HONO), which is generated in situ from a nitrate salt. The aniline is derived from the nitro compound via a reduction. The nitroaromatic is synthesized from the arene by electrophilic aromatic nitration, which is traditionally performed in nitric and sulfuric acids. Electrophilic nitration, like all electrophilic aromatic substitution reactions, is governed by electronics. Thus, certain functional groups (hydroxy, amino, alkoxy, alkyl, and halo) are ortho-/para-directing, while other functional groups (nitro, carboxy, and nitrilo) are meta-directing. Those experienced in the art will recognize the limitations of this approach in terms of product mixtures and the inability to access certain substitution patterns.

Another method for phenol synthesis involves the oxidation of an arylboronic acid or ester by means of hydrogen peroxide or OXONE. These methods require the pure boronic acid or ester as a starting material, which, in turn, are "traditionally" synthesized by a multi-step approach from an aryl halide. Again, those experienced in the art will recognize the limitations of this approach as it relies on electrophilic aromatic substitution to access the aryl halide.

A demonstrative example with 3-chloro-5-methylphenol will illustrate the inherent difficulties of the "traditional" approach and the benefit of this invention. As illustrated below, a "traditional" synthesis of 3-chloro-5-methylphenol might involve initial electrophilic chlorination of m-nitrotoluene to give a mixture of the desired 3-chloro-5-nitrotoluene and other isomers. Separation of the desired material from the other isomers by methods known to those experienced in the art would be followed by a reduction to give 3-chloro-5-methylaniline, which would then be converted into the diazonium salt and subsequently hydrolyzed to give 3-chloro-5-methylphenol.

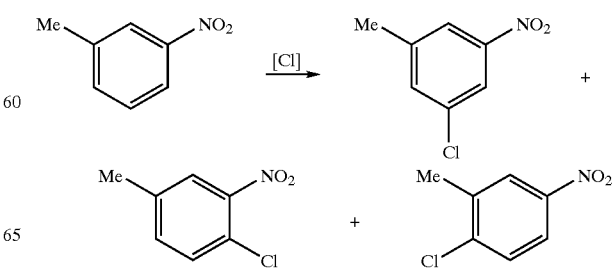

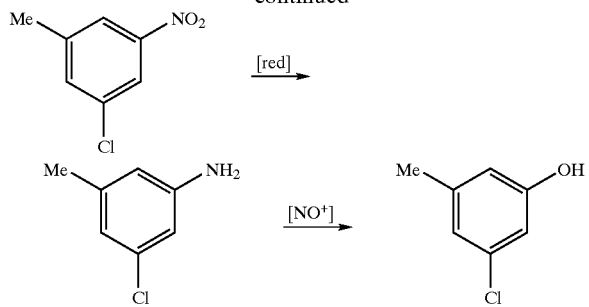

Alternative approaches involving electrophilic chlorination of 3-methylphenol or Friedel-Crafts alkylation of 3-chlorophenol, as illustrated below, would not give the desired phenol. Electrophilic aromatic substitution reactions on various arenes is shown below.

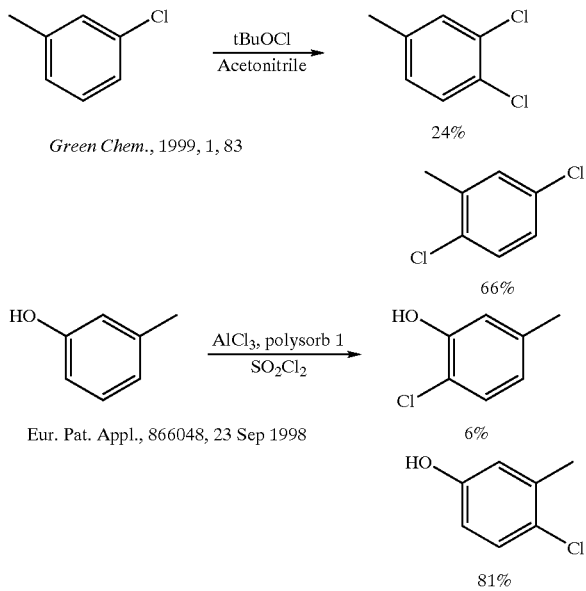

polysorb 1 = Benzene, diethenyl-, polymer with ethenylbenzene (9CI)

As can be seen, there remains a need for a process for synthesizing substituted phenols that is safer and less laborious than the prior art methods.

SUMMARY OF THE INVENTION

The present invention provides a process for producing a substituted phenol which comprises (a) reacting an arene with a borane selected from the group consisting of a borane with a B—H, B—B, and B—Si bond in the presence of a catalytically effective amount of an iridium or rhodium complex with three or more substituents, and with or without an organic ligand selected from the group consisting of phosphorus, carbon, nitrogen, oxygen, and sulfur organic ligands to produce an arylboronic ester; and (b) oxidizing the arylboronic ester with a hydrogenating oxidizing compound to produce the substituted phenol.

The present invention further provides a process for producing a substituted phenol which comprises (a) reacting in a reaction vessel an arene with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to produce an arylboronic ester; and (b) oxidizing the arylboronic ester formed in the reaction vessel with a hydrogenating oxidizing compound to produce the substituted phenol.

In a further embodiment of the above processes, the oxidizing compound is a peroxy compound selected from the group consisting of peroxymonosulfuric acid and salts thereof.

In a further embodiment, the oxidizing compound is taken from the group consisting of organic peroxides and salts thereof.

In a further embodiment of the above processes, the oxidizing agent is hydrogen peroxide.

In a further embodiment of the above processes, the oxidizing compound is an alkali metal peroxymonosulfate, preferably potassium peroxymonosulfate, most preferably $2KHSO_5 \cdot KHSO_4 \cdot K_2SO_4$.

In a further embodiment of the above processes, the iridium complex is selected from the group consisting of $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

In a preferred embodiment of the above processes, the iridium complex is (Ind)Ir(COD) wherein Ind is indenyl and COD is 1,5-cyclooctadiene.

In a preferred embodiment of the above processes, the organic ligand is a phosphorus organic ligand selected from the group consisting of trimethyl phosphine ($PMe_3$), 1,2-bis (dimethylphosphino)ethane (dmpe), and 1,2-bis (diphenylphosphino)ethane (dppe).

In a preferred embodiment of the above processes, the borane is pinacolborane (BPin).

In a preferred embodiment of the above processes, the substituted phenol has the general formula RR'R"Ar(OH) wherein R, R', and R" are each independently selected from the group consisting of hydrogen, halo, alkyl, alkoxy, carboxylic ester, amine, and amide and wherein Ar is selected from the group consisting of aryl and heteroaryl.

OBJECTS

The object of the present invention is to provide a process for producing substituted phenols which is easier, less costly, and safer than current processes.

DETAILED DESCRIPTION OF THE DRAWINGS

FIG. 1 shows the formulas for precatalysts 19 to 33. Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Figure 2:
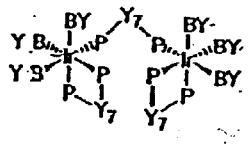
Figure 2:
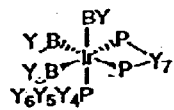
Figure 2:
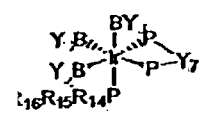
Figure 2:
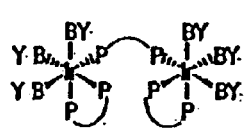
Figure 2:
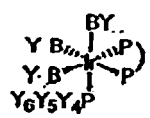
Figure 2:
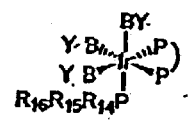
Figure 2:
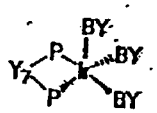
Figure 2:
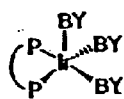
Figure 2:
Figure 2:
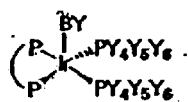
Figure 2:
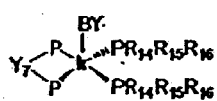
Figure 2:
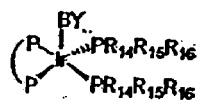

FIG. 2 shows the formulas for precatalysts 34 to 45. $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; (PY₇P) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons; (P⌒P) is of the formula

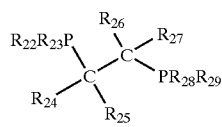

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; and BY is a boron moiety.

DETAILED DESCRIPTION OF THE INVENTION

All patents, patent applications, provisional patent applications, government publications, government regulations, and literature references cited in this specification are hereby incorporated herein by reference in their entirety. In case of conflict, the present description, including definitions, will control.

Phenols are common building blocks in the pharmaceutical industry. While many phenols are articles of commerce, the availability of specifically substituted phenols typically depends on if they can be accessed by traditional electrophilic aromatic substitution chemistry. For example, preparation of 3-chloro-5-methylphenol (Cevasco and Thea, J. Org. Chem. 61: 6814–6817 (1996)) (FIG. 1) has never appeared in the non-patent literature, while the only published route to 3-bromo-5-iodophenol requires many steps and employs TNT as the starting material (Hodgson and Wignall, J. Chem. Soc. 2077 (1926)).

Transition metal catalyzed C—H activations offer general solutions to the problem of synthesizing phenols since steric effects often dictate the regioselectivity of arene activation. Indeed, sterics dominate the regioselectivities for catalytic aromatic C—H activation/borylations (Cho et al., Science 295: 305–308 (2002) and references cited; Ishiyama et al., J. Am. Chem. Soc. 124: 390–391 (2002) and references cited), which effectively impart the chemical versatility of arylboronic acids and esters to aromatic C—H bonds. Moreover, the inventors have recently demonstrated that the functional group tolerance and selectivity of Ir catalysts enable the combination of such aromatic borylations with subsequent chemical events (Cho et al., Science 295: 305–308 (2002) and references cited). Since it is known that OXONE can oxidize arylboronic esters to phenols (Webb and Levy, Tetrahedron Lett. 36: 5117–5118 (1995)), we conceived that a one-pot aromatic C—H activation/borylation/oxidation protocol (Scheme 1) would constitute the most direct route to numerous structurally simple phenols whose practical use is currently limited by their accessibility.

Scheme 1

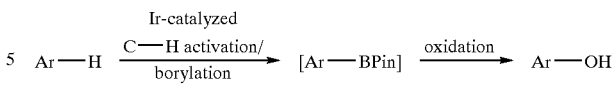

Iridium phosphine complexes catalyze the conversion of neat mixtures of arenes and pinacolborane (H—BPin) to arylboronic esters, where the arene is the limiting reagent (Cho et al., Science 295: 305–308 (2002) and references cited). Thus, we first attempted oxidation of arylboronic esters in crude reaction mixtures with OXONE using the literature protocol (OXONE, base, buffer, in 10–15% aqueous acetone at 2° C.) (Webb and Levy, Tetrahedron Lett. 36: 5117–5118 (1995)). Webb and Levy had disclosed a process for oxidizing arylboronic acids and esters to phenols using OXONE (Tetrahedron Lett. 36: 5117 (1995)). The reaction is complete within 10 minutes and gives the phenols in good to excellent yields (73–98%). The attempts to oxidize the arylboronic esters in the crude reaction mixtures gave irreproducible yields. Surprisingly, it was discovered that using a 1:1 acetone-water solution of OXONE and omitting the base and buffer gave good to excellent yields of substituted phenols at room temperature. In contrast, Webb and Levy had reported that performing OXONE oxidations above 15° C. gave lower yields.

Thus, the "one-pot" borylation/oxidation reaction of the present invention as generally described by Scheme 2 was created. The process enables the synthesis of once difficult to access phenols in one-pot from readily available starting materials.

Scheme 2

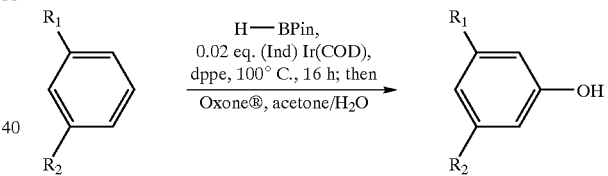

For example, the process of the present invention for producing 3-bromo-5-chlorophenol from 3-bromochlorobenzene (Scheme 3; Example 20) is an improvement over the prior art method illustrated in Scheme 4 in which the phenol is synthesized in 10 steps from 1,3,5-trinitrotoluene (TNT) (Hodgson and Wendall, J. Chem. Soc. 2077 (1926)).

Scheme 3

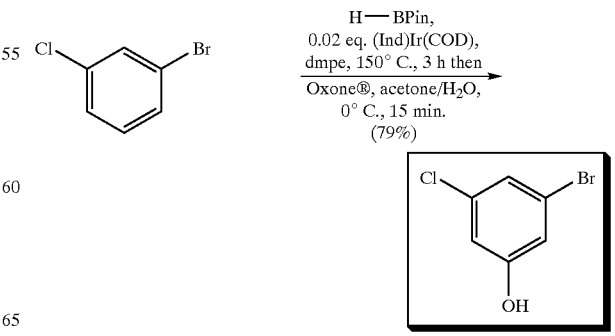

Scheme 4 (Prior art)

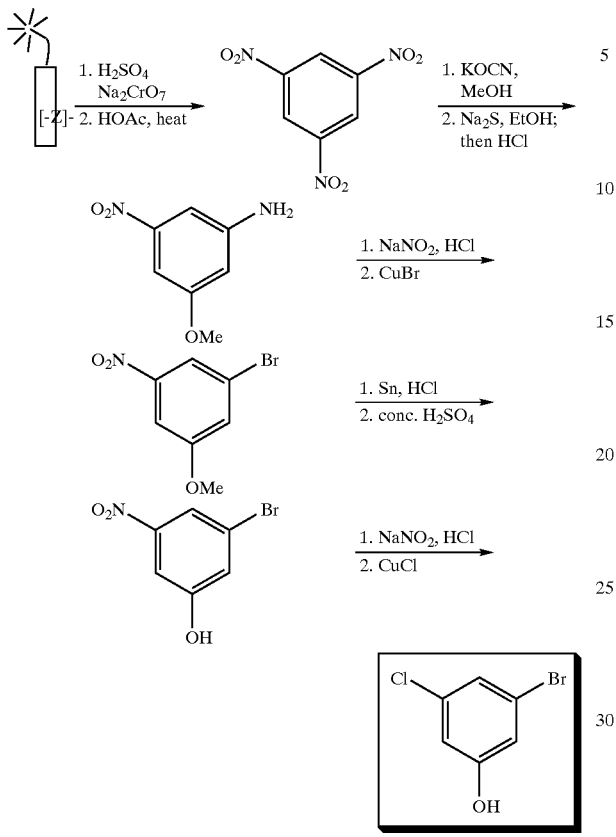

The chemistry shown herein illustrates what the process of the present invention can do for the pharmaceutical chemistry. Be it in a combinatorial setting or in process chemistry, telescoping traditional reaction sequences into a one pot process is a very attractive improvement over current processes. Thus, the process disclosed herein will greatly assist in the development of biologically significant compounds.

The typical process of the present invention consists of heating an H—BPin/arene mixture (HBPin:arene ~1.5–2.5:1) with (Ind)Ir(COD) (0.02 equiv. vs. arene) and 0.02 equiv. 1,2-bis(dimethylphosphino)ethane (dmpe) at 150° C. (or 1,2-bis(diphenylphosphino)ethane (dppe) at 100° C.)(Cho et al., Science 295: 305–308 (2002) and references cited)) until the borylation is complete by GC-FID. After the reaction mixture has cooled to room temperature, acetone and an aqueous solution of OXONE are added sequentially. Within about ten minutes stirring at room temperature the oxidation is usually complete, typically affording the phenol as the only aromatic product. As shown in Scheme 5, 3-bromo-5-chlorophenol (1) was prepared in 83% yield from commercially available 3-bromochlorobenzene. In contrast to the arduous route from TNT, the process herein can be completed in a single flask over the course of an afternoon.

Scheme 5

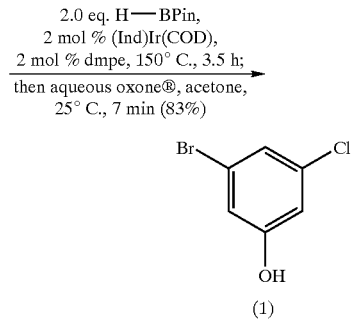

Thus, the present invention provides a process for the synthesis of a wide variety of substituted phenols such as those which have the general formula RR'R"Ar(OH) wherein R, R', and R" are each independently selected from the group consisting of hydrogen, halo, alkyl, alkoxy, carboxylic ester, amine, and amide and wherein Ar is selected from the group consisting of aryl and heteroaryl. In further embodiments, the substituted phenol has more than one hydroxyl group. The process involves the tandem regioselective borylation and oxidation in one pot of a substituted arene with any combination of non-interfering groups such as those of the general formula RR'R"Ar wherein R, R', and R" are each independently selected from the group consisting of hydrogen, halo, alkyl, alkoxy, carboxylic ester, amine, and amide and wherein Ar is selected from the group consisting of aryl and heteroaryl to produce the substituted phenols. The process greatly simplifies access to a variety of phenols and allows for the synthesis of previously undisclosed compounds. A key to the present invention is a result of the remarkable selectivity for the borylation of arenes. Unlike traditional electrophilic aromatic substitution, which is an integral element of "traditional" phenol syntheses and most often gives mixtures of products governed by electronics, the borylation element of the process of the present invention is governed by sterics and affords, in the present cases, single products.

In the first step, in a reaction vessel an arene substituted with any group which does not interfere with the borylation/oxidation reactions of the process is reacted with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to produce an arylboronic ester; and (b) oxidizing the arylboronic ester formed in the reaction vessel with hydrogenating oxidizing compound to produce the substituted phenol.

The oxidizing compound is preferably an alkali metal peroxymonosulfate, more preferably potassium peroxymonosulfate, and most preferably, the oxidizing compound comprises the triple salt $2KHSO_5 \cdot KHSO_4 \cdot K_2SO_4$ (potassium hydrogen peroxymonosulfate sulfate, CAS-RN 70693-62-8) of which potassium peroxymonosulfate or potassium monopersulfate salt ($K^{+-}O—S(=O)_2(—OOH)$ or $KHSO_5$), CAS-RN 10058-23-8 or 10361-76-9) is the active ingredient. $KHSO_5$ structurally resembles hydrogen peroxide or tert-butyl hydrogen peroxide. Potassium hydrogen peroxymonosulfate sulfate is commonly sold under the trademark OXONE (the trademark OXONE is owned by E.I. du Pont de Nemours and Company, Wilmington, Del.).

OXONE is well known to enable sulfones or sulfoxides to be prepared from sulfides (Trost et al., Tetrahedron Lett. 22: 1287–1290 (1981); Davis et al., J. Org. Chem. 53: 5004–5007 (1988)), oxides of both phosphorous (Wozniak et al., Tetrahedron Lett. 40: 2637–2640 (1999)) and nitrogen (Brik, Tetrahedron Lett. 36: 5519 (1995)), and several reports have shown that OXONE can also be used to oxidize aldehydes to carboxylic acids (Webb et al., Tetrahedron Lett. 54: 401–410 (1998); Baumstark et al., Tetrahedron Lett. 30: 5567–5570 (1989)). There are equivalents of OXONE such as potassium hydrogen peroxymonosulfate (CAS-RN 37222-66-5) available from Sigma, St. Louis, Mo., which can be used in the process of the present invention. The present invention embraces any alkali metal monopersulfate, in particular, wherein the metal is potassium, or to any peroxy compound selected from the group consisting of peroxymonosulfuric acid and salts thereof. Hydrogen peroxide or organic derivatives thereof also serve as oxidants.

Preferably, the B—C bond-forming reaction between a borane and an sp$^2$-hybridized C—H bond to produce a ring substituted arene in the first step is catalyzed by a catalyst comprising Ir or Rh in a complex with three or more substituents, preferably excluding hydrogen as a substituent, bonded to the Ir or Rh and further preferably, an organic ligand selected from the group consisting of phosphorus, carbon, nitrogen, oxygen, and sulfur organic ligands. Examples of ligands include, but are not limited to, phosphorus organic ligands, organic amines, imines, nitrogen heterocycles, ethers, and the like. Preferably, the ligand is in a molar ratio between about 1 to 3 and 1 to 1, wherein the organic ligand is at least in part bonded to the iridium or rhodium.

Effective precatalysts for forming the B—C bonds can be grouped into two families: those that contain cyclopentadienyl (CP*, $C_5R_5$ wherein R is $CH_3$) or indenyl (Ind, $C_9R_7$ wherein R is H) ligands and those that contain phosphine ligands. Included are compounds that contain both the Cp* and the Ind ligands and the phosphine ligands.

Preferably, the Ir catalytic composition for the first step of the process comprises one of the following: (ArH)Ir(BY)$_3$ wherein ArH is selected from the group consisting of aromatic, heteroaromatic, polyaromatic, and heteropolyaromatic hydrocarbon and wherein BY is a boron moiety; (MesH)Ir(BY)$_3$ wherein MesH is mesitylene and wherein BY is a boron moiety; (P(Y$_4$) (Y$_5$) (Y$_6$))$_3$Ir (H)$_n$(BY)$_{3-n}$ wherein Y$_4$, Y$_5$, and Y$_6$ are each selected from the group consisting of hydrogen, halide, alkyl, aryl, alkoxide (—O (R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure, wherein n is 0, 1, or 2, and wherein BY is a boron moiety; (P(R$_{14}$)(R$_{15}$)(R$_{16}$))$_3$Ir (H)$_n$(BY)$_{3-n}$ wherein R$_{14}$, R$_{15}$, and R$_{16}$ are each selected from the group consisting of hydrogen, linear alkyl, branched alkyl, and a carbon in a cyclic structure, wherein n is 0, 1, or 2, and wherein BY is a boron moiety; (P(Y$_4$) (Y$_5$) (Y$_6$))$_3$Ir (H) (R$_{13}$) (BY) wherein Y$_4$, Y$_5$, and Y$_6$ are as above, wherein R$_{13}$ is selected from the group consisting of a linear alkyl containing 1 to 8 carbon atoms, branched alkyl containing 1 to 8 carbons, aryl, and a carbon in a cyclic structure, and wherein BY is a boron moiety; (P(R$_{14}$) (R$_{15}$) (R$_{16}$))$_3$Ir (H) (R$_{17}$) (BY) wherein R$_{14}$, R$_{15}$, and R$_{16}$ are as above; R$_{17}$ is as above, and wherein BY is a boron moiety; {(PY$_7$P)Ir(BY)$_3$}$_2$($\mu_2$-(PY$_7$P)) (16) wherein BY is a boron moiety, wherein (PY$_7$P) is R$_{18}$R$_{19}$P—Y$_7$—PR$_{20}$R$_{21}$ wherein R$_{18}$, R$_{19}$, R$_{20}$, and R$_{21}$ are each selected from the group consisting of hydrogen, linear alkyl containing 1 to 8 carbon atoms, branched alkyl containing 1 to 8 carbons, and a carbon in a cyclic structure, and wherein Y$_7$ is a chain containing 1 to 12 carbons; (PY$_7$P)(P (Y$_4$) (Y$_5$) (Y$_6$))Ir(BY)$_3$ (17) wherein BY is a boron moiety, wherein Y$_4$, Y$_5$, and Y$_6$ are as above, and wherein (PY$_7$P) is as above; (PY$_7$P) (P(R$_{10}$)(R$_{11}$)(R$_{12}$))Ir(BY)$_3$ (18) wherein BY is a boron moiety, wherein R$_{14}$, R$_{15}$, and R1$_6$ are as above, wherein (PY$_7$P) is as above; {(P⌒P)Ir(BY)$_3$}$_2$($\mu_2$-(P⌒P)) (19) wherein BY is a boron moiety and wherein (P⌒P) is of the formula

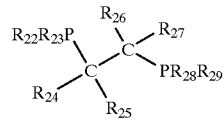

wherein R$_{22}$, R$_{23}$, R$_{24}$, R$_{25}$, R$_{26}$, R$_{27}$, R$_{28}$, and R$_{29}$ are each selected from the group consisting of alkyl chains, carbocyclic rings, and aryl groups; (P⌒P)(P(Y$_4$) (Y$_5$) (Y$_6$))Ir(BY)$_3$ (38) wherein BY is a boron moiety, wherein Y$_4$, Y$_5$, and Y$_6$ are as above, and wherein (P⌒P) is as above; (P⌒P) (P(R$_{14}$) (R$_{15}$) (R$_{16}$))Ir(BY)$_3$ (21) wherein BY is a boron moiety, wherein R$_{14}$, R$_{15}$, and R$_{16}$ are as above, and wherein (P⌒P) is as above; (PY$_7$P)Ir(BY)$_3$ (40) wherein BY is a boron moiety, and wherein and (PY$_7$P) is as above; (P⌒P)Ir(BY)$_3$ (23) wherein BY is a boron moiety, and wherein (P⌒P) is as above; (P(Y$_4$) (Y$_5$) (Y$_6$))$_4$Ir(BY) wherein Y$_4$, Y$_5$, and Y$_6$ are as above and BY is a boron moiety; (P(R$_{14}$)(R$_{15}$)(R$_{16}$))$_4$Ir (BY) wherein R$_{14}$, R$_{15}$, and R$_{16}$ are as above and BY is a boron moiety; (PY$_7$P) (P(Y$_4$) (Y$_5$) (Y$_6$))$_2$Ir(BY) (42) wherein BY is a boron moiety, wherein Y$_4$, Y$_5$, and Y$_6$ are above, and wherein (PY$_7$P) is as above; (P⌒P) (P(Y$_4$) (Y$_5$) (Y$_6$))$_2$Ir(BY) (43) wherein BY is a boron moiety, wherein Y$_4$, Y$_5$, and Y$_6$ are as above, and wherein (P⌒P) is as above; (PY$_7$P) (P(R$_{14}$)(R$_{15}$)(R$_{16}$))$_2$Ir(BY) (44) wherein BY is a boron moiety, R$_{14}$, R$_{15}$, and R$_{17}$ are as above, and wherein (PY$_7$P) is as above; (P⌒P)(P(R$_{14}$)(R$_{15}$)(R$_{16}$))$_2$Ir(BY) (45) wherein BY is a boron moiety, wherein R$_{14}$, R$_{15}$, and R$_{16}$ are as above, and wherein (P⌒P) is as above.

Examples of catalytic compositions comprising iridium include those selected from the group consisting of (Cp*)Ir (H)$_2$(Me$_3$P) (19), (Cp*)Ir(H) (BPin) (Me$_3$P) (20), (Cp*)Ir (H) (C$_6$H$_5$) (Me$_3$P) (21), (Ind)Ir(COD) (23), (MesH)Ir (BPin)(B(OR)$_2$) (27), ((R$_1$)$_3$P)$_3$Ir(B(OR$_2$)$_2$)$_3$ (28), (R$_1$)$_2$P)$_2$Ir(BPin)$_3$ (29), (((R$_1$)$_2$P)$_3$Ir((R$_2$O)$_2$B)$_3$)$_2$ (30), ((R$_1$)$_3$P)$_4$Ir (BPin) (31), ((R$_1$)$_2$P)$_2$Ir(BPin)$_3$ (32), (MesH)Ir(BPin)$_3$ (27 wherein B(OR)$_2$ is BPin), (IrCl(COD))$_2$ (33) and IrCl (COD), wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, R$_1$, and R$_2$ are each selected from the group consisting of hydrogen, linear or branched alkyl containing 1 to 8 carbons, aryl, and a carbon in a cyclic structure.

Preferably, the Rh catalytic composition for the first step comprises one of the following: (Cp') (P(Y$_4$) (Y$_5$) (Y$_6$))Rh (H)$_n$(BY)$_{2-n}$ wherein Y$_4$, Y$_5$, and Y$_6$ are as above, wherein n is 0 or 1, wherein BY is a boron moiety, and wherein Cp' is of the formula

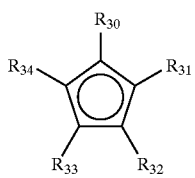

wherein $R_{30}$, $R_{31}$, $R_{32}$, $R_{33}$, and $R_{34}$ are each selected from the group consisting of hydrogen, alkyl chains, carbocyclic rings, and aryl groups; and (Cp') $(P(R_{14}(R_{15})\,(R_{16}))Rh(H)_n(BY)_{2-n}$ wherein $R_{14}$, $R_{15}$, and $R_{16}$ are as above; n is 0 or 1, wherein BY is a boron moiety; and wherein Cp' is as above.

Examples of catalytic compositions comprising rhodium include those selected from the group consisting of (Cp*)Rh(H)$_2$(Me$_3$P) (24), (Cp*)Rh(H) (BPin) (Me$_3$P) (25), (Cp*)Rh(H) (C$_6$H$_5$) (Me$_3$P) (26), and (Cp*)Rh (hexamethylbenzene) (22), wherein Cp* is 1,2,3,4,5-pentamethylcyclopentadienyl, BPin is pinacolborane, Me is methyl, H is hydrogen, and P is phosphorus.

In the above catalytic compositions, preferably the BY boron moiety selected from the group consisting of

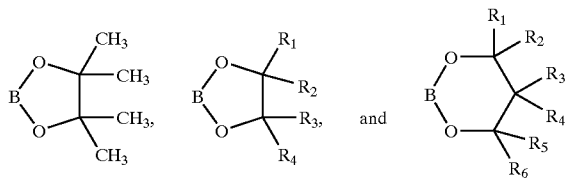

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure. Preferably, the borane is pinacolborane. FIGS. 1 and 2 show the structures of precatalysts 19 to 33 and 34 to 45, respectively.

Further examples of catalytic compositions, boranes, and substituted arenes which can be used in the process of the present invention can be found in U.S. patent application Ser. Nos. 10/194,809 and 10/194,859, both filed Jul. 12, 2002.

While the precatalysts can under particular reaction conditions catalyze the borylation of particular ring-substituted arenes, the reactions proceed more efficiently when an organic ligand such as phosphine ligands (phosphorus organic ligands) are included in the reaction mixture. The addition of phosphine ligands to the reaction generates active catalysts which can produce ring-substituted aryl boranes (aryl boronate esters and acids) with low catalyst loading. The fact that phosphine-containing species can catalyze borylation is important because numerous phosphines are commercially available. Furthermore, the selectivities of the borylation can be altered as a function of the phosphine ligand that is added. Examples of phosphine ligands include, but are not limited to, trimethyl phosphine (PMe$_3$), 1,2-bis(dimethylphosphino)ethane (dmpe), 1,2-bis (diphenylphosphino)ethane (dppe), Cy$_3$P, and Ph$_3$P.

Table 1 shows some of the phenols and the substrate from which they can be synthesized using the process of the present invention.

TABLE 1

| Substrate | Commercially Available | Phenol | Commercially Available | Refs. (total #) First Last |
|---|---|---|---|---|
| Cl-C$_6$H$_4$-Cl (1,3) | Yes | 3,5-dichlorophenol | Yes | (1127) J. Chromatogr. 25: 347 (1966); Anal. Chim. Acta 456: 41(2002) |
| 3-chlorotoluene | Yes | 3-chloro-5-methylphenol | No | (5) Ger. Offen DE2428157; Ger. Offen DE19918294 |
| 3-bromotoluene | Yes | 3-bromo-5-methylphenol | No | (14) J. Chem. Soc. Perkin 2: 32 (1981); WO 0121582 |
| 1,3-bis(trifluoromethyl)benzene | Yes | 3,5-bis(trifluoromethyl)phenol | Yes | (73) Chem. Pharm. Bull. 15: 1896 (1967); Jpn. Kokai Tokkyo Koho JP02080576 |

TABLE 1-continued

| Substrate | Commercially Available | Phenol | Commercially Available | Refs. (total #) First Last |
|---|---|---|---|---|
| 1,2-dichlorobenzene | Yes | 4,5-dichlorophenol | Yes | (1095) Can. J. Phys. Pharma. 62: 971 (1984); WO 0224663 |
| methyl 3-chlorobenzoate | Yes | methyl 3-chloro-5-hydroxybenzoate | No | (2) Heterocycles 23: 1483 (1985); WO 0020394 |
| 1-chloro-3-(trifluoromethyl)benzene | Yes | 3-chloro-5-(trifluoromethyl)phenol | No | No |
| 1,2-dimethoxybenzene | Yes | 3,4-dimethoxyphenol | Yes | (284) Takeda Kenkyusho Nempo 26: 138 (1967); WO 0202744 |
| 1-chloro-4-fluorobenzene | Yes | 4-chloro-2-fluorophenol | No | (1) Chem. Res. Toxicol. 10: 279 (1997) |
| 1-bromo-4-fluorobenzene | Yes | 4-bromo-2-fluorophenol | No | (6) EP238272; Ger. Offen DE19748819 |
| 3-methylanisole | Yes | 3-methyl-5-methoxyphenol | Yes | (69) Neth. Appl. NL 6716163; EP1172118 |
| 1-bromo-3-chlorobenzene | Yes | 3-bromo-5-chlorophenol | No | (1) J. Chem. Soc. 2077 (1926) |
| 1-bromo-3-iodobenzene | Yes | 3-bromo-5-iodophenol | No | (1) J. Chem. Soc. 2077 (1926) |
| 1,3-diiodobenzene | Yes | 3,5-diiodophenol | No | (2) Aust. J. Chem. 21: 1541 (1968); J. Am. Chem. Soc. 123: 5651 (2001) |

TABLE 1-continued

| Substrate | Commercially Available | Phenol | Commercially Available | Refs. (total #) First Last |
|---|---|---|---|---|
| 3,5-difluorobenzene (F, F, F) | Yes | 2,6-difluoro-4-hydroxy (OH, F, F, F) | Yes | (14) J. Water Pollut. Control Fed. 56: 1238 (1984); WO 0224663 |
| 1,3,5-trifluorobenzene | Yes | 2,4,6-trifluorophloroglucinol | No | No |
| 2,6-lutidine | Yes | 2,6-dimethyl-4-hydroxypyridine | Yes | (26) Rocz. Chem. 40: 1215 (1966); Jingxi Huagong 17: 149 (2000) |
| 2,6-dichloropyridine | Yes | 2,6-dichloro-4-hydroxypyridine | Yes | (4) J. Chem. Soc. B. 758 (1967); Polish J. Chem. 73: 1863 (1999) |
| 1,4-difluorobenzene | Yes | 2,5-difluorophenol | Yes | (51) Org. Magn. Reson. 9: 155 (1977); WO 0224663 |
| 1,3-dibromobenzene | Yes | 3,5-dibromophenol | No | (21) J. Chromatogr. 25:347(1966); WO 0204424 |
| 1,2-dibromobenzene | Yes | 3,4-dibromophenol | No | (8) J. Agric. Food Chem. 24: 291 (1976); Envir. Sci. Tech. 35: 3749 (2001) |
| 3-chloroanisole | Yes | 3-chloro-5-methoxyphenol | Yes | (20) Ger. Offen DE2720427 Chem. Res. Tox. 14: 1284 (2001) |
| 3-chloro-N,N-dimethylaniline | Yes | 3-chloro-5-(dimethylamino)phenol | No | No |

TABLE 1-continued
| Substrate | Commercially Available | Phenol | Commercially Available | Refs. (total #) First Last |
|---|---|---|---|---|
| 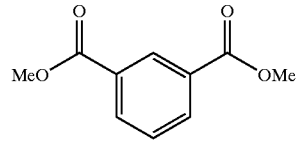 | Yes | 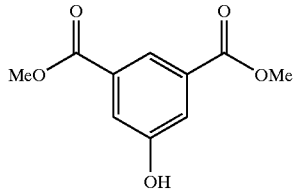 | Yes | (127) S. African ZA6706258; WO0224788 |
| 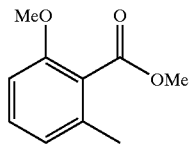 | No | 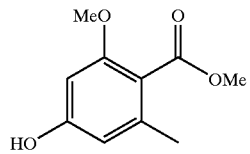 | No | (1) J. Med. Chem. 39: 5183 (1996) |
| 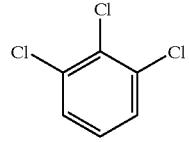 | Yes | 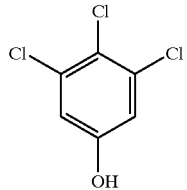 | Yes | (337) Spectrochim. Acta. (A), 24(12): 2059 (1968); Jpn Kokai Tokkyo Koho (2002) |
| 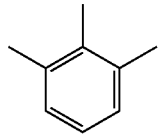 | Yes | 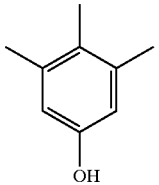 | Yes | (196) Neth. Appl. (1966); PCT Int. Appl. (2001) |
| 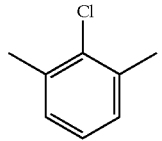 | Yes | 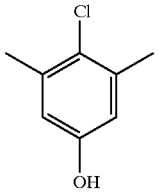 | Yes | (623) Medical Clinics of North Amer. 65(5): 1083 (1981); J. Health Sci. 48(1): 83 (2002) |
| 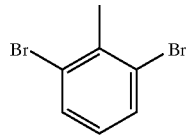 | Yes | 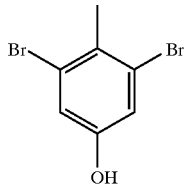 | Yes | (5) JACS 89(7): 1695 (1967); Environmental Sci. and Tech. 35(19) 3905 (2001) |
| 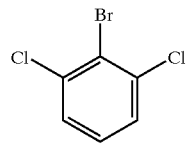 | Yes | 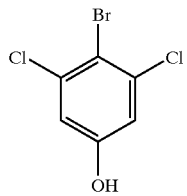 | Yes | (7) Takeda Kenkyusho Nempo 25: 109 (1966); PCT Int. Appl. (2001) |

TABLE 1-continued

| Substrate | Commercially Available | Phenol | Commercially Available | Refs. (total #) First Last |
|---|---|---|---|---|
| 2-bromo-1,3-dimethylbenzene | Yes | 4-bromo-3,5-dimethylphenol | Yes | (56) Zesz. Nauk. Uniw.Jagiellon/Pr. Chem.(9):215 (1964); Bioorg. And Medicinal Chem. Lett. 11(21): 2821 (2001) |
| 2-iodo-1,3-dimethylbenzene | Yes | 4-iodo-3,5-dimethylphenol | Yes | (11) Collect Czech Chem. Comm. 46(10): 2540 (1981); Jpn Kokai Tokkyo Koho (2002) |
| 1,3-dichloro-2-methoxybenzene | Yes | 3,5-dichloro-4-methoxyphenol | No | (5) Ger. Offen. (1975); Chemosphere 17(9): 1821(1988) |
| 1,3-dibromo-2-methoxybenzene | Yes | 3,5-dibromo-4-methoxyphenol | No | (5) JOC 31(11): 3666 (1966); Indian J. Chem.B 33B(2): 148 (1994) |
| 2-methoxy-1,3-dimethylbenzene | Yes | 4-methoxy-3,5-dimethylphenol | No | (5) Mem. Fac. Sci., Kyusho Univ., Ser. C 10(2): 133 (1977); Antcancer Drug Design 13(4): 1361 (1998) |
| 1,3-dichloro-2-methylbenzene | Yes | 3,5-dichloro-4-methylphenol | No | (7) Ger. Offen. (1975); Russian J. Org. Chem. 36(2): 254 (2000) |
| 2,3-dichloro-1-methoxybenzene | Yes | 3,4-dichloro-5-methoxyphenol | No | (1, all) U.S. (1988) |

TABLE 1-continued

| Substrate | Commercially Available | Phenol | Commercially Available | Refs. (total #)<br>First<br>Last |
|---|---|---|---|---|
| 3-chloro-2-methylphenyl (Cl, Cl, Me) | Yes | 3,4-dichloro-5-methylphenol (Cl, Cl, Me, OH) | No | (1, all)<br>Water Res.<br>18(12): 1545<br>(1984) |
| 3-chloro-2-methyl (Cl, Me) | Yes | 3-chloro-5-methylphenol (Cl, Me, OH) | No | (3)<br>Canada. J. Chem.<br>56(8): 1063<br>(1978);<br>Syn. 12: 1287<br>(1992) |
| 3-bromo-2-methyl (Br, Me) | Yes | 3-bromo-5-methylphenol (Br, Me, OH) | No | (6)<br>Perkin II 7:933<br>(1979);<br>J. Prakt. Chem./<br>Chem. Ztg.<br>340(2): 175<br>(1998) |
| 2-methyl-3-methoxy (Me, OMe) | Yes | 2-methyl-3-methoxy-5-hydroxy (Me, OMe, OH) | No | (2)<br>Syn. 12:1287<br>(1992);<br>J.Medicinal.<br>Chem. 39(21):<br>4181 (1996) |

The process of the present invention is not limited to synthesizing phenols having one hydroxy group as shown in Table 1. By adjusting the amounts of H—BPin and the oxidizing compound, multiple hydroxyls can be installed on the substrate. For examples, see entries 12–14 in Table 2.

In contrast to the prior art processes, the present invention allows for a much improved synthesis of substituted phenols such as 3-chloro-5-methylphenol. For example, as a non-limiting example, m-chlorotoluene is borylated using 2 mol % (Ind)Ir(COD), 2 mol % dmpe, and 1.5 equivalents of HBPin at 150° C. to afford 3-chloro-5-BPintoluene as the, only product. Without any manipulation of the material, an aqueous OXONE solution and an organic solvent are added. After a brief period, usually no more than 15 minutes, the reaction is quenched and the desired phenol is isolated as the single product by means known to those experienced in the art. This clearly represents a great improvement over the "traditional" approach.

The advantages of the present invention are that it provides direct access to phenols without need for intermediate purification, isolation, and characterization; thus, saving time, expense, money, and reducing hazardous waste. The present invention is an improvement over previous methods which are laborious, multi-step approaches, which use toxic and/or highly explosive materials as starting materials. For an example, several halogenated phenols were previously synthesized from trinitrotoluene via a long multi-step approach (Hodgson and Wignall, J. Chem. Soc. 2077 (1926)).

Other metals and/or ligands can be used to perform the borylation. Other boranes can be utilized in the borylation. The OXONE oxidation can be performed in the absence of $NaHCO_3$ and/or NaOH. Other oxidants, like hydrogen peroxide, can be used for the oxidation.

The following examples are intended to promote a further understanding of the present invention.

EXAMPLES 1–18

This example illustrates the synthesis of a variety of substituted phenols using the process of the present invention.

Table 2 summarizes the syntheses of various other phenols using the process of the present invention. As previously noted (Cho et al., Science 295: 305–308 (2002) and references cited; Ishiyama et al., J. Am. Chem. Soc. 124: 390–391 (2002) and references cited), electron-donating substituents retard aromatic borylations, but subsequent oxidations of the resulting arylboronic esters and the isolated yields of the corresponding phenols were not visibly perturbed by electronic effects. That said, for electron-poor phenols, complete removal of hydrogen bond accepting solvents such as acetone or ether required distillation or sublimation (See below for full details). Improvements over published routes were realized for most of the known phenols in Table 2 (See below for full details). Moreover, preparations of phenols 7 and 14–17 are described here for the first time. Perhaps most noteworthy, aromatic borylation/oxidation appears to be the first unified approach to 1–18.

Over oxidation (Magdziak et al., Org. Lett. 4: 285–288 (2002) and references cited; Crandall et al., Tetrahedron Lett. 32: 5441–5444 (1991)) was not a problem, as quinones were not observed. Even for substrates bearing oxidizable nitrogens, such as the pyridine of Entry 5 and the amino group of Entry 16, no N-oxides were detected in the isolated products (Preliminary spectroscopic studies suggest that transient amounts of N-oxides are being formed during these reactions). Ethers and esters could survive the transformation (Entries 3–4), but demethylation of 2,6-dichloroanisole (Entry 8) accompanied borylation (Demethylation of 2,6-dichloroanisole is known to be facile. See Majetich et al., Tetrahedron Lett. 47: 8727–8730 (1994)). The small Van der Waals radius of fluoride makes possible the preparation of 5-bromo-2-fluorophenol (13). Furthermore, multiple hydroxyls can be installed by adjusting the amounts of H—BPin and OXONE (Entries 12–13).

Borylations can also be performed in inert solvents such as cyclohexane (Entries 5, 9–11, 13–15), which is then removed prior to the oxidation step. The oxidation step can be performed in other water miscible solvents such as acetonitrile, DMF, dioxane, THF, or diglyme. Thus, while acetone remains the preferred solvent for the oxidation step, dimethyldioxirane is not a required intermediate. In situ formation of DMDO when acetone is the solvent has not been ruled out. However, the reactions are run in the absence of base or buffer, which are typically added to promote DMDO formation (See Webb and Levy, Tetrahedron Lett. 36: 5117–5118 (1995); Murray, Chem. Rev. 89: 1187–1201 (1989)). Furthermore, a reaction using DMDO in place of aq. OXONE only afforded a trace of the phenol. Oxidations in $CHCl_3$ or $CH_2Cl_2$ failed. In contrast, 3,4-dichlorophenol was obtained in 44% yield when $Bu_4NI$ (25 mol %) was added to an oxidation run in $CH_2Cl_2$.

While bromide and chloride tolerance were universal, partial deiodination of 1-bromo-3-iodobenzene occurred during borylation with (Ind)Ir(COD). This can be avoided by using Ishiyama and Miyaura's $[Ir(OMe)(COD)]_2$-d$^t$bpy system to borylate with $B_2Pin_2$ at room temperature (Scheme 6) (Ishiyama et al., Angew. Chem. Int. Ed. 41: 3056–3058 (2002)).

Scheme 6

In summary, the one-pot aromatic borylation/oxidation of the present invention is an efficient protocol for preparing phenols. This method is particularly attractive for the generation of meta-substituted phenols bearing ortho/para-directing groups; as such substrates are often difficult to access by other means.

TABLE 2

Phenols via one-pot C—H activation/borylation/oxidation.[a]

| entry | starting arene | H—BPin equiv. | borylation time (h)[b] | phenol | % yield[c] |
|---|---|---|---|---|---|
| 1[d,e,f] | Br, Br (disubstituted benzene) | 2.0 | 18 | Br, Br, OH (2) | 87 |
| 2 | Br, Me | 1.5 | 12 | Br, Me, OH (3) | 81 |
| 3 | Cl, MeO | 2.0 | 18 | Cl, MeO, OH (4) | 79 |

TABLE 2-continued

Phenols via one-pot C—H activation/borylation/oxidation.[a]

| entry | starting arene | H—BPin equiv. | borylation time (h)[b] | phenol | % yield[c] |
|---|---|---|---|---|---|
| 4[d] | 3-chloro methyl benzoate (MeO2C, Cl) | 1.5 | 3 | methyl 3-chloro-5-hydroxybenzoate (MeO2C, Cl, OH) (5) | 70 |
| 5[d,g] | 2,6-dichloropyridine | 1.5 | 3 | 2,6-dichloro-4-hydroxypyridine (6) | 64 |
| 6 | 2,3-dichlorotoluene (Cl, Cl, Me) | 2.0 | 12 | (Cl, Cl, Me, OH) (7) | 85 |
| 7 | 2,6-dichlorotoluene (Cl, Me, Cl) | 1.5 | 12 | (Cl, Me, Cl, OH) (8) | 88 |
| 8 | 2,6-dichloroanisole (Cl, MeO, Cl) | 2.5 | 16 | (Cl, HO, Cl, OH) (9) | 68 |
| 9[f,g] | 3-bromo-o-xylene (Br, Me, Me) | 2.5 | 50 | (Br, Me, Me, OH) (10) | 72 |
| 10[g] | 2-bromo-1,3-dichlorobenzene (Cl, Br, Cl) | 2.0 | 3.5 | (Cl, Br, Cl, OH) (11) | 80 |
| 11[g] | 1,2,3-trichlorobenzene (Cl, Cl, Cl) | 1.8 | 3 | (Cl, Cl, Cl, OH) (12) | 89 |

TABLE 2-continued

Phenols via one-pot C—H activation/borylation/oxidation.[a]

| entry | starting arene | H—BPin equiv. | borylation time (h)[b] | phenol | % yield[c] |
|---|---|---|---|---|---|
| 12 | 4-Br, 1-F benzene | 0.25 | 3.5 | 4-Br, 3-F, 1-OH, 2-F phenol (13) | 68 |
| 13[e,g] | 4-Br, 1-F benzene | 4.5 | 53 | Br, HO, OH, F substituted phenol (14) | 74 |
| 14[d,e,g] | 1,3,5-trifluorobenzene | 5.0 | 63 | HO, F, F, OH, HO, F hexasubstituted (15) | 51 |
| 15[g] | 3-Cl, 1-CF$_3$ benzene | 1.5 | 3.5 | Cl, CF$_3$, OH phenol (16) | 80 |
| 16[e] | 3-Me$_2$N, 1-Cl aniline | 2.0 | 18 | Me$_2$N, Cl, OH phenol (17) | 79 |

[a]Typical conditions: Arene, H—BPin, 2 mol % (Ind)Ir(COD), 2 mol % dmpe, neat under N$_2$; then acetone, 1 equiv. (per boron) aqueous OXONE, 25° C., 7 min (see below for details).
[b]Borylation time can be H—BPin batch dependent.
[c]Average isolated yields of two runs.
[d]The borylation was described in Cho et al., Science 295: 305–308 (2002) and references cited.
[e]See below for slight deviation from typical conditions.
[f]Borylation run with dppe at 100° C.
[g]Borylation run in C$_6$H$_{12}$.

The method for synthesizing phenols 1–18 was as follows.

All substrates were subject to purification before use. Solid substrates were sublimed under vacuum. Liquid substrates were stirred or refluxed, depending on the boiling points, over Na, CaH$_2$, or molecular sieves (4 Å) overnight, distilled, and degassed. Cyclohexane was purchased from Aldrich, washed with concentrated H$_2$SO$_4$ until the acid layer was colorless. Water and saturated NaHCO$_3$ solution washes then followed until the water wash was neutral. The cyclohexane was then dried over MgSO$_4$ before being refluxed over Na, distilled, and degassed. n-Hexane was purchased from Baker Inc., refluxed over Na, distilled, and degassed. Pinacolborane (H—BPin) was purchased from Aldrich, stirred over PPh$_3$ overnight, vacuum transferred into an air-free flask and brought into a dry box. B$_2$Pin$_2$ was purchased from Frontier Scientific Discovery Chemicals and used without purification. 1,2-Bis(dimethylphosphino)-ethane (dmpe) and 1,2-bis(diphenylphosphino)ethane (dppe) were purchased from Strem and d$^t$pby (4,4'-di-tert-butyl-2,2'-bipyridine) from Aldrich. These ligands were used as received. (Ind)Ir(COD) (Ind=indenyl, COD=1,5-cyclooctadiene) and [Ir(OMe)(COD)]$_2$ were prepared per literature procedures (Tyman, Synthetic and Natural Phenols; Elsevier: New York, (1996); Hanson et al., J. Chem. Soc., Perkin Trans 2: 1135–1150 (2002); George et al., J. Chem. Soc., Perkin Trans 1: 2529–2574 (2000); Sweeney, Contemp. Org. Synth. 4: 435–453 (1997)). OXONE was purchased from Aldrich as 2KHSO$_5$.KHSO$_4$.K$_2$SO$_4$ and was used as a ~0.3 mol/L aqueous solution. Reagent grade acetone was purchased from CCI and used without purification. Technical grade acetone also worked well.

All borylation reactions were carried out in oven-dried thick-walled air-free flasks, magnetically stirred, and monitored by Varian CP-3800 GC-FID (column type: WCOT Fused silica 30 m*0.25 mm ID coating CP-SIL 8 CB). Silica gel was supplied by Silicycle as 60 Å (230–400 Mesh). Yields refer to isolated material and have been corrected to discount the added weight of trapped residual solvent. All spectral data reported was obtained from solvent free material. Infrared spectra were obtained on a Nicolet IR/42 spectrometer; $^1$H NMR and $^{13}$C NMR spectra were recorded on a Varian Gemini-300 or a Varian VXP-500 spectrometer (300, 500 MHz for $^1$H, respectively, and 75, 125 MHz for $^{13}$C, respectively), with chemical shifts reported relative to the residue peaks of solvent chloroform ($\delta$ 7.24 for $^1$H and 77.0 for $^{13}$C) or acetone ($\delta$ 2.04 for $^1$H and 29.8 for $^{13}$C). Melting points were measured on a Thomas-Hoover capillary melting point apparatus and are uncorrected; GC-MS were recorded by HP 5890 Series II GC with SPB-1 non-polar column, in series with a Trio-1 mass spectrometer; high-resolution mass spectra were obtained at Michigan State University Mass Spectrometry Service Center with a JOEL-AX505 mass spectrometer (resolution 7000); preparative GC was performed with a Varian 920 GC-TCD with packed $C_{18}$ column. Combustion analyses were performed on a Perkin Elmer Series II 2400 CHNS/O analyzer.

The general borylation/oxidation process of the present invention was as follows. The general process for borylations was as follows. In a dry box, arene (1.0 mmol), HBPin (1.5–2.5 mmoles), (Ind)Ir(COD) (8.3 mg, 0.02 mmol, 2 mol %), and dmpe (3.0 mg, 0.02 mmol, 2 mol %). or dppe (8.0 mg, 0.02 mmol, 2 mol %) were transferred into an air-free flask equipped with a stirrer bar. (In cases where cyclohexane was used as a solvent, the reagents were dissolved in 1 mL cyclohexane, and transferred to the air-free flask.) The flask was sealed and brought out of the dry box and placed in an oil bath heated to 150° C. (dmpe) or 100° C. (dppe) until the reaction was judged complete by GC—FID. At that time the reaction was allowed to cool to room temperature. If solvent was used it was removed under reduced pressure.

The general process for oxidations was as follows. To the crude material from above (usually a dark orange or brown gel-like liquid or a solid) was added 3.2 mL acetone. After stirring produced a homogeneous solution, an aqueous solution of OXONE (6.15 g, 1.0 mmol in 3.2 mL) was added dropwise over 2–4 min. Upon complete addition, the reaction mixture was vigorously stirred for 7 minutes. At that time the reaction was quenched with aqueous $NaHSO_3$. A layer of dark orange oil was observed. The reaction mixture was extracted three times with ether or $CH_2Cl_2$. The combined organics were washed with brine followed by water, and concentrated in vacuo. The crude material was dissolved in $CH_2Cl_2$ or pentane/ether and passed through a plug of silica gel. Evaporation afforded the phenol. (Note: In the cases of multiple borylations (Tables 1, Entries 15–16), periodic cooling and purging of the $H_2$ gas formed during that step of the sequence helped to maintain an effective rate of reaction.)

Experimental details for synthesizing particular phenols, their spectroscopic data, and comparisons to previous methods are provided below.

3-Bromo-5-chlorophenol (1): The general process was applied to 3-bromochlorobenzene (192 mg, 1.0 mmol). The borylation step was carried out neat with HBPin (250 mg, 1.95 mmol) and dmpe (3.0 mg, 0.02 mmol, 2 mol %) at 150° C. for 3.5 hours. The oxidation step was then carried out as described above, after which the crude material was dissolved in $CH_2Cl_2$ and passed through a plug of silica gel. Evaporation of solvent gave 183 mg of a white solid containing 171 mg (82%) of 1 and 12 mg of trapped acetone (by $^1$H NMR). Preparative GC at 160° C. afforded analytically pure 1 as a white solid; mp 66–68° C. (lit. 70). $^1$H NMR (300 MHz, $CDCl_3$): $\delta$ 7.08 (t, J=1.65 Hz, 1 H), 6.89 (dd, J=2.2, 1.65 Hz, 1 H), 6.78 (t, J=2.1 Hz, 1 H), 5.0–5.1 (brs, 1 H); $^{13}$C NMR (75 MHz, $CDCl_3$): $\delta$ 156.7, 135.6, 124.0, 122.9, 117.9, 115.0; IR (neat): 3293, 1578, 1435, 914, 775 $cm^{-1}$; LRMS m/e 206 ($M^+$), 127, 99. Anal. Calcd for $C_6H_4BrClO$: C, 34.74; H, 1.94. Found C, 34.87; H 2.03. For a previous preparation of 1 see either Hodgson and Wignall, J. Chem. Soc. 2077–2079 (1926) (ten steps from 1,3,5-trinitrotoluene, overall yield not reported) or Kohn and Zandman, Montash. 47: 367–377 (1926) (exhaustive bromination of 3-chlorophenol, followed by partial debromination).

3,5-Dibromophenol (2): The general process was applied to a solution of 1,3-dibromobenzene (236 mg, 1.0 mmol) in 1.0 mL cyclohexane. The borylation step was carried out with HBPin (256 mg, 2 mmol) and dppe (8.0 mg, 0.02 mmol, 2 mol %) at 100° C. for 18 hours. After removal of cyclohexane, the oxidation step was then performed as described above, after which the crude material was dissolved in $CH_2Cl_2$ and passed through a plug of silica gel. Evaporation of solvent gave 250 mg material containing 227 mg phenol 2 (90%), 12 mg water, and 11 mg acetone (by $^1$H NMR). Sublimation at 55° C. under 0.08 mm Hg afforded analytically pure 2 as a white solid; mp 78–80° C. (lit. 81). $^1$H NMR (300 MHz, $CDCl_3$): $\delta$ 7.23 (t, J=1.4 Hz, 1 H), 6.94 (d, J=1.4 Hz, 2 H), 4.82 (s, 1 H); $^{13}$C NMR (75 MHz, $CDCl_3$): $\delta$ 156.7, 126.7, 123.1, 117.8; IR (neat): 3233, 1576, 1421, 841, 752 $cm^{-1}$; LRMS: m/e 250 ($M^+$), 171, 143. Anal. Calcd for $C_6H_4Br_2O$: C, 28.61; H, 1.60. Found C, 28.98; H, 1.52. For a previous preparation see Ishida et al., Polymers for Adv. Tech. 11: 698–704 (2000) (debromination of pentabromophenol, 76% yield).

3-Bromo-5-methylphenol (3): The general process was applied to 3-bromotoluene (171 mg, 1.0 mmol). The borylation step was carried out neat with HBPin (200 mg, 1.55 mmol) and dmpe (3.0 mg, 0.02 mmol, 2 mol %) at 150° C. for 12 hours. The oxidation step was then performed as described above, after which the crude material was dissolved in $CH_2Cl_2$ and passed through a plug of silica gel. Evaporation of solvent gave 174 mg material containing 146 mg phenol 3 (78%), 11 mg $CH_2Cl_2$, and 17 mg acetone. Preparative GC at 150° C. afforded analytically pure 3 as a white solid; mp 55–57° C. (lit. 52). $^1$H NMR (300 MHz, $CDCl_3$): $\delta$ 6.89 (s, 1 H), 6.80 (s, 1 H), 6.56 (s, 1 H), 4.67 (s, 1 H), 2.26 (s, 3 H); $^{13}$C NMR (75 MHz, $CDCl_3$) $\delta$ 156.0, 141.4, 124.7, 122.4, 115.8, 115.0, 21.1; IR (neat): 3297, 1579, 1366, 1273, 822 $cm^{-1}$; LRMS: m/e 186 ($M^+$), 107, 77. Anal. Calcd for $C_7H_7BrO$: C, 44.95; H, 3.77. Found C, 45.21; H, 3.93. For a previous preparation see Brittain et al., J. Chem. Soc., Perkin Trans. 2: 32–41 (1981) (four steps from 3-methylphenol, overall yield not reported).

3-Chloro-5-methoxyphenol (4): The general process was applied to 3-chloroanisole (143 mg, 1.0 mmol). The borylation step was carried out neat with HBPin (256 mg, 2 mmol) and dmpe (3.0 mg, 0.02 mmol, 2 mol %) at 150° C. for 18 hours. The oxidation step was then performed as described above, after which the crude material was dissolved in $CH_2Cl_2$ and passed through a plug of silica gel. Evaporation of solvent gave 148 mg material containing 121 mg phenol 4 (76%), 7 mg $CH_2Cl_2$, and 20 mg acetone. Preparative GC at 170° C. afforded analytically pure 4 as a white solid; mp 94–96° C.[8] $^1$H NMR (300 MHz, $CDCl_3$): $\delta$ 6.48 (t, J=2.2 Hz, 1 H), 6.43 (t, J=2.2 Hz, 1 H), 6.27 (t, J=2.2

Hz, 1 H), 4.81 (s, 1 H), 3.75 (s, 3 H); $^{13}$C NMR (75 MHz, CDCl$_3$): δ 161.3, 157.0, 135.4, 108.6, 107.3, 100.4, 55.5; IR (neat): 3378, 1597, 1159 cm$^{-1}$; LRMS: m/e 158 (M$^+$), 128. Anal. Calcd for C$_7$H$_7$ClO$_2$: C, 53.02; H, 4.45. Found C, 52.88; H, 4.81. Another preparation of this compound was reported by Testaferri et al., Tetrahedron 39: 193–197 (1983) as a byproduct during the reaction of NaOMe with 1,3,5-trichlorobenzene, 7% yield, no mp reported.

Methyl 3-Chloro-5-hydroxybenzoate (5): The general process was applied to methyl 3-chlorobenzoate (171 mg, 1.0 mmol). The borylation step was carried out neat with HBPin (200 mg, 1.55 mmol) and dmpe (3.0 mg, 0.02 mmol, 2 mol %) at 150° C. for 3 hours. The oxidation step was then performed as described above, after which the crude material was dissolved in ether and passed through a plug of silica gel (pentane/ether 2:1). Evaporation of solvent gave 134 mg phenol 5 (72%) with trace water. Sublimation at 85° C. under 0.06 mm Hg afforded analytically pure 5 as a white solid; mp 133–135° C. (lit. 138–139). $^1$H NMR (300 MHz, acetone-d$_6$): δ 9.2 (brs, 1 H), 7.43 (t, J=1.7 Hz, 1 H), 7.40 (dd, J=2.2, 1.7 Hz, 1 H), 7.10 (t, J=2.2 Hz, 1 H), 3.87 (s, 3 H); $^{13}$C NMR (75 MHz, acetone-d$_6$): δ 165.9, 159.3, 135.3, 133.8, 121.0, 120.6, 115.7, 52.7; IR (neat): 3335, 1690, 1591, 1431, 1350, 1242, 768 cm$^{-1}$; LRMS: m/e 186 (M$^+$), 155, 127, 99. Anal. Calcd for C$_8$H$_7$ClO$_3$: C, 51.50; H, 3.78. Found C, 51.78; H, 3.73. For a previous preparation see Takahashi et al., Heterocycles 23: 1483–1491 (1985) (three steps from 3,5-dichlorobenzoic acid, 65% overall yield).

2,6-Dichloro-4-pyridinol (6): The general process was applied to 2,6-dichloropyridine (148 mg, 1.0 mmol). The borylation step was carried out with HBPin (200 mg, 1.55 mmol, 1.55 equiv.) and dmpe (3.0 mg, 0.02 mmol, 2 mol %) at 150° C. in cyclohexane for 3 hours (Ir-catalyzed borylation of the arene was previously described, see Cho et al., Science 295: 305–308 (2002)). The oxidation step was then performed after removal of cyclohexane as described above, after which the crude material was dissolved in ether and passed through a plug of silica gel (pentane/ether 2:1). Evaporation of solvent gave 145 mg material containing 108 mg phenol 6 (66%) and 37 mg water. Sublimation at 110° C. under 0.1 mmHg afforded analytically pure 6 as a white solid; mp 201–202° C. $^1$H NMR (300 MHz, acetone-d$_6$): δ 10.48 (brs, 1 H), 6.88 (s, 2 H); $^{13}$C NMR (75 MHz, acetone-d$_6$): δ 168.3, 151.5, 111.5; IR (KBr): 3200~2500 (br), 1597, 1576, 1554, 1427, 1294, 1211, 1157, 1092, 993, 966, 847 cm$^{-1}$; LRMS: m/e 163 (M$^+$), 128, 100. Anal. Calcd for C$_5$H$_3$Cl$_2$NO: C, 36.62; H, 1.84; N, 8.54. Found C, 36.63; H, 1.98, N, 8.52. Another preparation of this compound was reported by Umemoto et al., Bull. Chem. Soc. Jpn. 64: 1081–1092 (1991) as a byproduct (mp not reported) during the hydrolysis of an N-fluoro-2,6-dichloropyridinium PF$_6^-$ salt that was prepared by the reaction of 2,6-dichloropyridine with F$_2$ gas with a 4% yield.

3,4-Dichloro-5-methylphenol (7): The general process was applied to 2,3-dichlorotoluene (161 mg, 1.0 mmol). The borylation step was carried out neat with HBPin (256 mg, 2 mmol) and dmpe (3.0 mg, 0.02 mmol, 2 mol %) at 150° C. for 12 hours. The oxidation step was then performed as described above, after which the crude material was dissolved in CH$_2$Cl$_2$ and passed through a plug of silica gel. Evaporation of solvent gave 154 mg material containing 147 mg phenol 7 (83%) and 7 mg water. Sublimation at 70° C. under 0.07 mmHg afforded analytically pure 7 as a white solid; mp 98–100 ° C. $^1$H NMR (300 MHz, CDCl$_3$): δ 6.81 (d, J=2.2 Hz, 1 H), 6.63 (t, J=2.2 Hz, 1 H), 4.61 (s, 1 H), 2.34 (s, 3 H); $^{13}$C NMR (75 MHz, CDCl$_3$): δ 153.7, 139.1, 133.0, 124.3, 116.4, 115.0, 21.3; IR (neat): 3285, 1580, 1449, 1285, 1151, 886, 646 cm$^{-1}$; LRMS: m/e 176 (M$^+$), 141, 77. Anal. Calcd for C$_7$H$_6$Cl$_2$O: C, 47.49; H, 3.42. Found C, 47.72; H, 3.61. No other preparation of this compound appears to have been reported, however, it has been used in water treatment experiments (Ben Amor et al., Water Res. 18: 1545–1516 (1984)).

3,5-Dichloro-4-methylphenol (8): The general process was applied to 2,6-dichlorotoluene (161 mg, 1.0 mmol). The borylation step was carried out neat with HBPin (200 mg, 1.55 mmol) and dmpe (3.0 mg, 0.02 mmol, 2 mol %) at 150° C. for 12 hours. The oxidation step was then performed as described above, after which the crude material was dissolved in CH$_2$Cl$_2$ and passed through a plug of silica gel. Evaporation of solvent gave 176 mg material containing 156 mg phenol 8 (88%), 14 mg water, and 6 mg acetone. Sublimation at 70° C. under 0.08 mmHg afforded analytically pure 8 as a white solid; mp 92–93° C. $^1$H NMR (300 MHz, CDCl$_3$): δ 6.79 (s, 2 H), 4.67 (s, 1 H), 2.34 (s, 3 H); $^{13}$C NMR (75 MHz, CDCl$_3$): δ 153.5, 135.6, 126.6, 115.2, 16.4; IR (neat): 3333, 1608, 1578, 1238, 947, 839 cm$^{-1}$; LRMS: m/e 176 (M$^+$), 141, 105, 84, 77. Anal. Calcd for C$_7$H$_6$Cl$_2$O: C, 47.49; H, 3.42. Found C, 47.65; H, 3.45. For a previous preparation see Wedemeyer, K.; Koppelmann, E. Ger. Offen. DE2344926 (1975) (three steps from 4-methylphenol, 54% yield, mp not reported). This example shows that for substrates which comprise an oxymethyl group flanked by halogens, the oxymethyl group is oxidized to a hydroxy group.

2,6-Dichloro-1,4-hydroquinone (9): The general process was applied to 2,6-dichloroanisole (177 mg, 1.0 mmol). The borylation step was carried out neat with HBPin (320 mg, 2.5 mmol) and dmpe (3.0 mg, 0.02 mmol, 2 mol %) at 150° C. for 16 hours. The oxidation step was then performed, after which the crude material was dissolved in ether and passed through a plug of silica gel (pentane/ether 2:1). Evaporation of solvent gave 140 mg material containing 120 mg hydroquinone 9 (67%) and 20 mg water. Sublimation at 90° C. under 0.08 mmHg or recrystallization from CH$_2$Cl$_2$ afforded analytically pure 9 as a white solid; mp 160–161° C. (lit. 164). $^1$H NMR (300 MHz, acetone-d$_6$): δ 8.43 (brs, 1 H), 8.24 (brs, 1 H), 6.83 (s, 2 H); $^{13}$C NMR (75 MHz, acetone-d$_6$): δ 150.7, 142.3, 122.3, 115.5; IR (KBr): 3349, 1591, 1482, 1213, 953, 791 cm$^{-1}$; LRMS: m/e 178 (M$^+$), 142, 114, 86. Anal. Calcd for C$_6$H$_4$Cl$_2$O$_2$: C, 40.26; H, 2.25. Found C, 40.58; H, 2.17. For a previous preparation see Kulkarni and Kate, J. Chem. Soc., Perkin. Trans. 1: 4242–4244 (2000) (photoreduction of 2,6-dichloro-1,4-benzoquinone with a vitamin C derivative, 87% yield). This material is also available from Apin.

3-Bromo-4,5-dimethylphenol (10): The general process was applied to a solution of 3-bromo-o-xylene (185 mg, 1.0 mmol) in 1.0 mL cyclohexane. The borylation step was carried out with HBPin (320 mg, 2.5 mmol) and dppe (8.0 mg, 0.02 mmol, 2 mol %) at 100° C. for 50 hours. After removal of the cyclohexane, the oxidation step was then performed as described above, after which the crude material was dissolved in CH$_2$Cl$_2$ and passed through a plug of silica gel. Evaporation of solvent gave 148 mg pure 10 (74%) as a white wax solid; mp 98–99° C. (lit. 101–102). $^1$H NMR (300 MHz, CDCl$_3$): δ 6.91 (d, J=2.5 Hz, 1 H), 6.59 (d, J=2.7 Hz, 1 H), 2.25 (s, 6 H); $^{13}$C NMR (75 MHz, CDCl$_3$): δ 153.2, 139.3, 128.3, 125.2, 116.9, 116.2, 21.4, 18.3; IR (neat): 3252, 2919, 1606, 1576, 1477, 1451, 1279, 1119, 839 cm$^{-1}$; LRMS: m/e 200 (M$^+$), 185, 121, 91; HRMS (EI): m/z 199.9839 [(M$^+$); calcd for C$_8$H$_9$BrO: 199.9837]. For a previous preparation see Jacquesy et al., Chem. Soc., Chem. Commun. 110–111 (1980) (bromination of 3,4- dimethylphenol in superacid SbF$_5$-HF, 83% yield) or Fischer and Henderson, Can. J. Chem. 61: 1045–1052 (1983).

4-Bromo-3,5-dichlorophenol (11): The general process was applied to a solution of 1-bromo-2,6-dichlorobenzene (226 mg, 1.0 mmol) in 1.0 mL cyclohexane. The borylation step was carried out with HBPin (256 mg, 2 mmol, 2 equiv.) and dmpe (3.0 mg, 0.02 mmol, 2 mol %) at 150° C. for 3.5 hours. After removal of solvent, the oxidation step was then performed as described above, after which the crude material was dissolved in CH$_2$Cl$_2$ and passed through a plug of silica gel. Evaporation of solvent gave 260 mg material containing 197 mg phenol 11 (81%), 31 mg CH$_2$Cl$_2$, and 32 mg acetone. Sublimation at 90° C. under 0.30 mmHg afforded analytically pure 11 as a white solid; mp 117–119° C. $^1$H NMR (300 MHz, CDCl$_3$): δ 6.90 (s, 2 H), 4.86 (s, 1 H); $^{13}$C NMR (75 MHz, CDCl$_3$): δ 154.8, 136.5, 116.2, 114.4; IR (neat): 3366, 1570, 1412, 1129, 845 cm$^{-1}$. LRMS: m/e 240 (M$^+$), 162; HRMS (EI): m/z 239.8751 [(M$^+$); calcd for C$_6$H$_3$Cl$_2$BrO: 239.8744]. For a previous preparation see Soma and Konishi, Takeda Kenkyusho Nenpo 25: 109–122 (1996) (two steps of 3,5-dichloroaniline, overall yield or mp not reported).

3,4,5-Trichlorophenol (12): The general process was applied to a solution of 1,2,3-trichlorobenzene (182 mg, 1.0 mmol) in 1.0 mL cyclohexane. The borylation step was carried out with HBPin (226 mg, 1.8 mmol) and dmpe (3.0 mg, 0.02 mmol, 2 mol %) at 150° C. for 3 hours. After removal of solvent, the oxidation step was then performed as described above, after which the crude material was dissolved in CH$_2$Cl$_2$ and passed through a plug of silica gel. Evaporation of solvent gave 212 mg material containing 176 mg phenol 12 (89%), 4 mg CH$_2$Cl$_2$, and 32 mg acetone. Sublimation at 70° C. under 0.06 mmHg afforded analytically pure 12 as a white solid; mp 97–99° C. (lit. 101). $^1$H NMR (300 MHz, CDCl$_3$): δ 6.89 (s, 2 H), 5.04 (s, 1 H); $^{13}$C NMR (75 MHz, CDCl$_3$): δ 154.0, 134.4, 123.3, 116.3; IR (neat): 3312, 1574, 1420, 1144, 947, 818 cm$^{-1}$; LRMS: m/e 196 (M$^+$), 160, 133, 97. Anal. Calcd for C$_6$H$_3$Cl$_3$O: C, 36.50; H, 1.53. Found C, 36.73; H, 1.64. For a previous preparation see Miles, GB13116277 (1973) (byproduct of the reaction of 1,2,3,5-tetrachlorobenzene with NaOH, 3.3% yield, mp not reported). This material is also available from AccuStandard or Sigma-Aldrich.

5-Bromo-2-fluorophenol (13): The general process was applied to 1-bromo-4-fluorobenzene (700 mg, 4.0 mmol). The borylation step was carried out neat with HBPin (128 mg, 1.0 mmol) and dmpe (3.0 mg, 0.02 mmol, 2 mol %) at 150° C. for 3.5 hours. The oxidation step was then performed as described above, after which the crude material was dissolved in CH$_2$Cl$_2$ and passed through a plug of silica gel. The first fraction collected contained ~500 mg unreacted arene. Evaporation of the second fraction gave 165 mg of material containing 134 mg phenol 13 (70%; H—BPin limiting reagent), 17 mg CH$_2$Cl$_2$, and 14 mg acetone. Preparative GC at 110° C. afforded analytically pure 13 as a colorless oil. $^1$H NMR (300 MHz, CDCl$_3$): δ 7.12–7.16 (m, 1 H), 6.90–6.96 (m, 2 H), 5.29 (s, 1 H); $^{13}$C NMR (125 MHz, CDCl$_3$): δ 150.3 (d, T=239 Hz), 144.4 (d, J=15 Hz), 123.7 (d, J=6 Hz), 120.6, 116.8 (d, J=19 Hz), 116.8 (d, J=3 Hz); IR (neat): 3412, 1611, 1495, 1267 cm$^{-1}$; LRMS: m/e 190 (M$^+$), 161, 111, 83. Anal. Calcd for C$_6$H$_4$BrFO: C, 37.73; H, 2.11. Found C, 37.58; H, 2.32. For a previous preparation see Elliott et al., GB2187731 (1987) (three steps from 2,4-dibromofluorobenzene, 18% overall yield).

5-Bromo-2-fluororesorcinol (14): The general process was applied to a solution of 1-bromo-4-fluorobenzene (175 mg, 1.0 mmol) in 1.0 mL cyclohexane. The borylation step was carried out with HBPin (580 mg, 4.5 mmol, 4.5 equiv.), (Ind)Ir(COD) (20.6 mg, 0.05 mmol, 5 mol %) and dppe (20.0 mg, 0.05 mmol, 5 mol %) at 110° C. for 53 hours. After removal of solvent, the oxidation step was then performed utilizing 6.5 mL acetone, 6.5 mL aqueous OXONE (12.4 g in 6.5 mL, 2 equiv.) at room temperature for 11 min. The crude material was subsequently dissolved in ether and passed through a plug of silica gel (pentane/ether 1.5:1). After evaporation of solvent, the crude product was recrystallized from CH$_2$Cl$_2$, giving 165 mg 14 (76%) as a white solid; mp 83–86° C. R$_f$ 0.31 (pentane/ether 2:1). $^1$H NMR (300 MHz, CDCl$_3$): δ 6.72 (d, J=7.1 Hz, 2 H), 5.10 (s, 2 H); $^{13}$C NMR (75 MHz, acetone-d$_6$): δ 147.5 (d, J=11 Hz), 141.4 (d, J=237 Hz), 115.8 (d, J=5 Hz), 112.3; IR (KBr): 3128, 1617, 1501, 1431, 1331, 1159, 1047 cm$^{-1}$. LRMS: m/e 206 (M$^+$), 127, 109, 79; HRMS (EI): m/z 205.9378 [(M$^+$); calcd for C$_6$H$_4$BrFO$_2$: 205.9379]. This example shows that multiple BPin substitutions followed by oxidation to hydroxy groups can be performed in a single reaction.

2,4,6-Trifluoroglucinol (15): The general process was applied to a solution of 1,3,5-trifluorobenzene (132 mg, 1.0 mmol) in 1.0 mL cyclohexane. The borylation step was carried out with HBPin (640 mg, 5 mmol), (Ind)Ir(COD) (12.5 mg, 0.03 mmol, 3 mol %) and dmpe (4.5 mg, 0.03 mmol, 3 mol %) at 150° C. for 63 hours. The borylation gives a 1:6 mixture of diborylated and triborylated products. After removal of solvent, the mixture was subjected to the oxidation using 9 mL acetone, 8.5 mL aqueous OXONE (17.4 g in 8.5 mL, 2.8 equiv.) at room temperature for 13 min. The crude material was subsequently dissolved in ether and passed through a plug of silica gel (pentane/ether 1:1.5). After evaporation of solvent, the crude product was washed with boiling CH$_2$Cl$_2$ and then sublimed at 130° C. under 0.1 mmHg, giving 88 mg 15 (49%) as a slightly yellow solid; mp 260° C. (decomposed). R$_f$ 0.43 (pentane/ether 1:1.5). $^1$H NMR (300 MHz, acetone-d$_6$): δ 8.66 (brs, 3 H); $^{13}$C NMR (125 MHz, acetone-d$_6$): δ 137.3 (dt, J=230, 6 Hz) 131.9 (dt, J=14, 5 Hz); IR (KBr): 3324, 1510, 1400–1200 (br), 1132, 980 cm$^{-1}$; LRMS: m/e 180 (M$^+$), 151, 104; HRMS (EI): m/z 180.0030 [(M$^+$); calcd for C$_6$H$_3$F$_3$O$_3$: 180.0034]. It appears that no other preparation of this compound has been reported.

3-Chloro-5-trifluoromethylphenol (16): The general process was applied to a solution of 3-chlorobenzotrifluoride (181 mg, 1.0 mmol) in 1.0 mL cyclohexane. The borylation step was carried out with HBPin (200 mg, 1.55 mmol) and dmpe (3.0 mg, 0.02 mmol, 2 mol %) at 150° C. for 3.5 hours. After removal of solvent, the oxidation step was performed as described above, after which the crude material was dissolved in CH$_2$Cl$_2$ and passed through a plug of silica gel. Evaporation of solvent gave 185 mg material containing 160 mg phenol 16 (81%) and 25 mg acetone. Preparative GC at 120° C. afforded analytically pure 16 as a colorless oil. R$_f$ 0.34 (CH$_2$Cl$_2$). $^1$H NMR (300 MHz, CDCl$_3$): δ 7.18 (brs, 1 H), 7.01 (brs, 1 H), 6.96 (brs, 1 H), 5.03 (s, 1 H); $^{13}$C NMR (75 MHz, CDCl$_3$): δ 156.5, 135.7, 133.1 (q, J=33 Hz), 123.0 (q, J=273 Hz), 119.2, 118.5 (q, J=4 Hz); IR (KBr): 3384, 1597, 1455, 1335, 1175, 1134, 936 704, 693 cm$^{-1}$; LRMS: m/e 196 (M$^+$), 177, 161, 146; HRMS (EI): m/z 195.9902 [(M$^+$); calcd for C$_7$H$_4$ClF$_3$O: 195.9903]. It appears that no other preparation of this compound has been reported.

3-Chloro-5-(dimethylamino)phenol (17): The general process was applied to 3-chloro-N,N-dimethylaniline (156 mg, 1.0 mmol). The borylation step was carried out neat with HBPin (256 mg, 2 mmol) and dmpe (3.0 mg, 0.02 mmol, 2 mol %) at 150° C. for 18 hours. The oxidation step was then performed at 0° C. for 15 min. The crude material was then passed through a plug of silica gel (pentane/ether 2:1). Evaporation of solvent gave 155 mg material containing 146 mg phenol 17 (85%) and 9 mg ether. Sublimation at 60° C. under 0.10 mmHg afforded analytically pure 17 as a slightly colored solid; mp 86–88° C. $R_f$ 0.30 (pentane/ether, 2:1). $^1$H NMR (300 MHz, CDCl$_3$): δ 6.28 (brs, 1 H), 6.19 (t, J=1.6 Hz, 1 H), 6.03 (t, J=2.2 Hz, 1 H), 5.0–5.3 (brs, 1 H), 2.88 (s, 6 H); $^{13}$C NMR (75 MHz, CDCl$_3$): δ 156.8, 152.3, 135.4, 105.6, 104.2, 97.8, 40.4; IR (neat): 3349, 2901, 2812, 1603, 1506, 1443, 1156, 1233, 1019, 916 cm$^{-1}$; LRMS: m/e 171 (M$^+$), 170, 128, 99. Anal. Calcd for C$_8$H$_{10}$ClNO: C, 55.99; H, 5.87; N, 8.16. Found C, 56.12; H, 5.81; N, 8.11. It appears that no other preparation of this compound has been reported.

3-Bromo-5-iodophenol (18): To a solution of 1-bromo-3-iodobenzene (283 mg, 1 mmol) in 5 mL n-hexane, was added B$_2$Pin$_2$ (154 mg, 0.6 mmol, 1.2 equiv. boron), [Ir(OMe)(COD)]$_2$ (10.0 mg, 0.015 mmol, 1.5 mol %), and d$^t$bpy (8.0 mg, 0.03 mol, 3 mol %) (Ishiyama et al., Angew. Chem. Tnt. Ed. 41: 3056–3058 (2002)). The mixture was stirred at room temperature for 11 hours. After removal of hexane, the oxidation step was performed as described above. The reaction was extracted with Et$_2$O (CH$_2$Cl$_2$ is to be avoided). After evaporation of the ethereal layer, the crude material was dissolved in CH$_2$Cl$_2$ and passed through a plug of silica gel. Evaporation of solvent gave 244 mg of a solid material containing 236 mg phenol 18 (79%), 5 mg ether, and 3 mg acetone. Sublimation at 50° C. under 0.09 mmHg afforded analytically pure 18 as a white solid; mp 83–84° C. (lit. 82.5). $^1$H NMR (300 MHz, CDCl$_3$): δ 7.42 (t, J=1.4 Hz, 1 H), 7.13 (dd, J=1.4, 2.2 Hz, 1 H), 6.96 (dd, J=1.9, 2.2 Hz, 1 H), 4.77 (s, 1 H); $^{13}$C NMR (75 MHz, CDCl$_3$): δ 156.4, 132.4, 123.6, 123.2, 118.6, 94.2; IR (neat): 3268, 3071, 1586, 1566, 893, 885, 664 cm$^{-1}$; LRMS: m/e 298 (M$^+$), 171, 143. Anal. Calcd for C$_6$H$_4$BrIO: C, 24.11; H, 1.35. Found C, 24.26; H, 1.30. For a previous preparations see Hodgson and Wignall, J. Chem. Soc. 2077–2079 (1926) (ten steps from TNT, overall yield not reported).

EXAMPLE 19

A representative, but non-limiting, oxidation process for the synthesis of 3-bromo-5-chlorophenol is shown below.

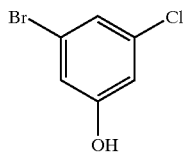

To an airfree flask equipped with a stir bar, in a glove box, was added m-bromochlorobenzene (192 mg, 1.00 mmol), HBPin (200 mg, 1.56 mmol), (Ind)Ir(COD) (8.3 mg, 0.02 mmol), and dmpe (3.0 mg, 0.02 mmol). The flask was sealed, removed for the glove box, and stirred at 150° C. for 3 h. This material was used in next step without purification. To the crude material was added NaOH (1.5 mL of a 1.5M aqueous solution) and the resulting mixture was stirred for 5 minutes. To this was added NaHCO$_3$ (0.73 g, 8.7 mmol) and acetone (3 mL). The mixture was cooled to 0° C. and OXONE (3.2 mL of a 0.33M aqueous solution) was added dropwise. The reaction mixture was stirred at 0° C. for 10 minutes and quenched with sodium bisulfite (2.0 g in 3 ml H$_2$O). The grayish solution was diluted with ether (20 ml), and extracted with aq. 2 M HCl (1×25 ml). The aqueous layer was separated from the organic layer and extracted with ether (2×25 ml). Combined organic layers were washed with water (2×25 ml), dried with MgSO$_4$, and solvents removed under reduced pressure. Crude material was passed through silica plug eluting with CH$_2$Cl$_2$ to give 163.4 mg (78.8%) of 3-bromo-5-chlorophenol as a white solid. In a separate run under the same conditions with twice the scale, 301.2 mg (72.4%) of desired phenol was obtained. mp=68–69° C. $^1$H NMR (CDCl$_3$, 300 MHz) δ 7.08 (t, J=1.65 Hz, 1H), 6.89 (dd, J=2.2, 1.65 Hz, 1H), 6.78 (dd, J=2.2, 1.65 Hz, 1H), 4.83 (s, 1H). $^{13}$C NMR (CDCl$_3$, 125 MHz) δ 156.6, 135.7, 124.1, 122.9, 117.4, 115.0. FT-IR (KBr) 3221, 3159, 3090, 3046, 2927, 2856, 2793, 2659, 2492, 1577, 1486, 1458, 1426, 1376, 1359, 1286, 1239, 1214, 1088, 913, 859, 840, 778, 666 cm$^{-1}$. MS (rel. int.) m/z 208 (100), 206 (82), 127 (26), 99 (37), 63 (22). Anal. Calcd for C$_6$H$_4$BrClO: C, 34.74; H, 1.94; N, 0.00. Found: C, 35.08; H, 2.03; N, 0.07.

EXAMPLES 20–25

This example shows a general process for synthesizing various substituted phenols using the process of the present invention.

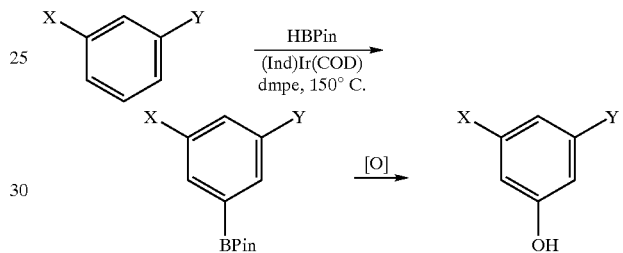

The general process was as follows.

Borylation: In a dry box filled with nitrogen, an air-free flask, previously dried thoroughly in oven, was charged with a stirrer bar, 1 mmol arene, 0.02 mmol (2 mol %) Ir catalyst, 0.02 mmol (2 mol %) dmpe, followed by 1.5 mmol HBPin (Amounts of catalyst, dmpe and HBPin vary according to substrates). The flask was tightly sealed and was put into 150° C. oil bath for selected period of time, then cooled to room temperature.

Oxidation condition A was as follows. The borylation mixture in the air free flask was vigorously stirred. To this mixture was added 1.5 mL 1.5 M aqueous NaOH, followed by 5 min stirring. Then 0.73 g NaHCO$_3$ was added followed by 4.7 ml acetone. The mixture was cooled by an ice bath, and 3.2 mL 0.33 M aqueous OXONE was added slowly. After 12–15 min of stirring, the reaction was quenched by NaHSO$_3$.

Oxidation condition B (no NaHCO$_3$) was as follows. The borylation mixture in the air free flask was vigorously stirred. To this mixture was added 1.5 mL 1.5 M aqueous NaOH, followed by 5 min stirring. Then 4.7 ml acetone was added. The mixture was then cooled by an ice bath, and 3.2 mL 0.33 M aqueous OXONE was added slowly. After 12–15 min of stirring, the reaction was quenched by NaHSO$_3$.

Oxidation condition C (no NaOH) was as follows. The borylation mixture in the air free flask was vigorously stirred. To this mixture was added 3.0–3.5 ml acetone and 3–5 min were allowed to stir. The mixture was then cooled by an ice bath, and 3.2 mL 0.33 M aqueous OXONE was added slowly. After 12–15 min of stirring, the reaction was quenched by NaHSO$_3$.

Oxidation condition D (no ice bath) was as follows. The borylation mixture in the air free flask was vigorously stirred. To this mixture was added 3.0–3.5 ml acetone and 3–5 min were allowed to stir. Then 3.2 mL 0.33 M aqueous OXONE was added dropwise at room temperature. After 7 min of stirring, the reaction was quenched by $NaHSO_3$.

In the oxidation, the preferred acetone/water ratio is about 1:1. While other solvents can be used in the oxidation, acetone is presently the preferred solvent.

The workup process was as follows. To the mixture after oxidation, dichloromethane or ether was added to extract the formed phenol with the acidification of the whole mixture. The organic layer was separated and washed with brine, dried over $MgSO_4$, and vacuumed to remove the solvent. The residue was allowed to pass through a silica plug, and the phenol was obtained. Most phenols, especially those with an electron-poor arene ring, are trapping acetone, or ether if ether was used in the workup process.

The chemistry background was as follows. Selectivity: 1,3-disubstituted arene was borylated on the double-meta position, forming a 3,5-disubstituted phenol. Symmetric 1,2-disubstituted arene was borylated on 4 position, forming a 3,4-disubstituted phenol. 1,2,3-trisubstituted arene was borylated on 5 position, forming a 3,4,5-trisubstituted phenol. Fluorine-substituted arene can be borylated on positions ortho to F.

Functional group tolerances were as follows. Halide, ether, dialkyl amine, ester, alkyl groups are tolerated. Aldehyde and ketone carbonyls are reduced as well as nitrile. In some instances, acidic protons can be problematic. The results are shown in Table 3.

TABLE 3

| Entry | Arene Substrate | Phenol Product | Borylation | Oxid Cond | Ylds % |
|---|---|---|---|---|---|
| 1 | 1,3-dichlorobenzene | 3,5-dichlorophenol | 3–3.5 h | A<br>B<br>C<br>D | 81<br>78<br>78<br>74 |
| 2 | 3-chloro-bromobenzene | 3-bromo-5-chlorophenol | 2 eq. HBPin, 3–3.5 h | B | 80, ~85 |
| 3 | 4-bromo-fluorobenzene | 5-bromo-2-fluorophenol | 4 eq. arene 3.5–4 h | B | 70, 72 |
| 4 | 3-trifluoromethyl-chlorobenzene | 3-chloro-5-trifluoromethylphenol | 4–4.5 h, in cyclohexane | B<br>D | 78<br>78 |
| 5 | Meta-xylene | 3,5-dimethylphenol | 4 mol % "Ir" and dmpe, 2.5 eq HBPin, 24 h | C | 57, 54 |

TABLE 3-continued

| Entry | Arene Substrate | Phenol Product | Borylation | Oxid Cond | Ylds % |
|---|---|---|---|---|---|
| 6 | 3-bromotoluene | 3-bromo-5-methylphenol | Overnight, 11–12 h | A<br>B<br>C | 75<br>76,<br>80,<br>83<br>78 |

In view of the above, a highly selective and effective process for converting an arene to its corresponding phenol has been developed. The reactions are fast and efficient.

EXAMPLES 26–27

This Example shows the synthesis of the following phenols using the one-pot borylation/oxidation reaction of the present invention.

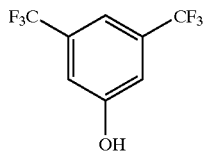

3,5-Bis(trifluoromethyl)phenol was synthesized as follows. The general process was applied to 1,3-bis(trifluoromethyl)benzene (214 mg, 1.0 mmol). The borylation step was carried out neat with HBPin (200 mg, 1.55 mmol, 1.55 equiv.) and dmpe (3.0 mg, 0.02 mmol, 2 mol %) at 150° C. for 3.5 hours. The oxidation step was then performed as described above, afterwhich the crude material was dissolved in CH$_2$Cl$_2$ and passed through a plug of silica gel. Evaporation of solvent gave 218 mg material containing 189 mg of the phenol (82%), 4 mg CH$_2$Cl$_2$ and 25 mg acetone. Passing through prepGC at ~120° C. afforded the analytically pure product as a colorless oil. $^1$HNMR (300 MHz, CDCl$_3$): δ 7.44 (brs, 1 H), 7.25 (brs, 2 H), 5.23 (s, 1 H); $^{13}$CNMR (125 MHz, CDCl$_3$): δ 156.2, 133.2 (q, J=33 Hz), 123.0 (q, J=273 Hz), 115.9, 114.7 (Sept, J=3~4 Hz); IR (neat): 3613, 3443, 1464, 1387, 1281, 1177, 1134, 939 cm$^{-1}$. LRMS: m/e 230 (M$^+$), 211, 210, 180, 161, 132, 113; HRMS: anal. calcd for C$_8$H$_4$F$_6$O: 230.0166; found 230.0165. Previous preparation was two steps from 1,3-bis(trifluoromethyl)benzene in 45% yield, (Porwisiak and Schlosser, Chem. Ber. 129: 233–5 (1996).

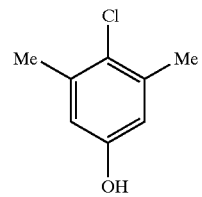

4-Chloro-3,5-dimethylphenol was synthesized as follows. The general process was applied to 2-chloro-m-xylene (141 mg, 1.0 mmol). The borylation step was carried out neat with HBPin (320 mg, 2.5 mmol, 2.5 equiv.) and dmpe (3.0 mg, 0.02 mmol, 2 mol %) at 150° C. for 18 hours. The oxidation step was then performed as described above, afterwhich, the crude material was dissolved in CH$_2$Cl$_2$ and passed through a plug of silica gel. Evaporation of solvent gave 147 mg material containing 130 mg of the phenol (83%) and 17 mg water. Sublimation at 80° C. under 0.10 mmHg afforded the analytically pure product as a slightly yellow solid; mp 112~113° C. $^1$HNMR (300 MHz, CDCl$_3$): δ 6.55 (s, 2 H), 4.45 (s, 1 H), 2.30 (s, 6 H); $^{13}$CNMR (75 MHz, CDCl$_3$): δ 153.2, 137.4, 126.2, 115.2, 20.8; IR (neat): 3291, 1590, 1488, 1318, 1167 cm$^{-1}$. LRMS: m/e 156 (M$^+$), 121, 91. Anal. Calcd for C$_8$H$_9$ClO: C, 61.35; H, 5.79. Found C, 61.57; H, 5.98.

EXAMPLES 28–29

The general process was used to make the following two phenols. 3-methyl-5-chlorophenol was made 3-methyl-chlorobenzene with 72% yield and 1,2-dimethoxyphenol

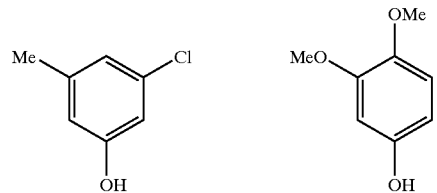

was made from 1,2-dimethoxybenzene with 58% yield.

EXAMPLE 30

By following the general process but substituting DMF for acetone in the oxidation reaction, 1,2-dichlorophenol was made from 1,2-dichlorobenzene with 85% yield.

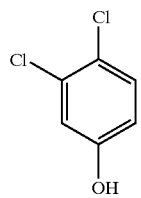

EXAMPLE 31

By following the general process but using the B$_2$Pin$_2$, [Ir(OMe)(COD)]$_2$, under dtbpy borylation conditions, 3,5-dibromo-4-iodophenol was made from 2-iodo-1,3-bromobenzene with 92% yield.

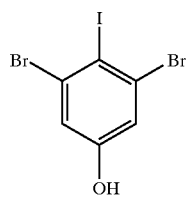

The 3,5-dibromo-4-indophenol was recently used by Yamada et al. (J. Am. Chem. Soc. 125: 6630–6631 (2003)) in a synthesis of the antitumor antibiotics duocarmycins. However, their synthesis of the phenol required five separate operations starting from p-nitrophenol. In contrast, the process herein used two operations. First, the conversion of 2,6-dibromoaniline to the 2-iodo-1,3-dibromobenzene and second, the one-pot borylation/oxidation process of the present invention to make the 3,5-dibromo-4-iodophenol.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for producing a substituted phenol which comprises:
   (a) reacting an arene with a borane selected from the group consisting of a borane with a B—H, B—B, and B—Si bond in the presence of a catalytically effective amount of an iridium or rhodium complex with three or more substituents, and with or without an organic ligand selected from the group consisting of phosphorus, carbon, nitrogen, oxygen, and sulfur organic ligands to produce an arylboronic ester; and
   (b) oxidizing the arylboronic ester with a hydrogenating oxidizing compound to produce the substituted phenol.

2. The process of claim 1 wherein the oxidizing compound is a peroxy compound selected from the group consisting of peroxymonosulfuric acid and salts thereof.

3. The process of claim 1 wherein the oxidizing compound is an alkali metal peroxymonosulfate.

4. The process of claim 3 wherein the alkali metal peroxymonosulfate is potassium peroxymonosulfate.

5. The process of claim 1 wherein the oxidizing compound is $2KHSO_5 \cdot KHSO_4 \cdot K_2SO_4$.

6. The process of claim 1 wherein the oxidizing compound is an organic peroxide.

7. The process of claim 1 wherein the oxidizing compound is hydrogen peroxide.

8. The process of claim 1 wherein the iridium complex is selected from the group consisting of $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B))_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

9. The process of claim 1 wherein the iridium complex is $(Ind)Ir(COD)$ wherein Ind is indenyl and COD is 1,5-cyclooctadiene.

10. The process of claim 1 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

11. The process of claim 1 wherein the borane is pinacolborane (BPin).

12. The process of claim 1 wherein the substituted phenol has the general formula RR'R"Ar(OH) wherein R, R', and R" are each independently selected from the group consisting of hydrogen, halo, alkyl, alkoxy, carboxylic ester, amine, and amide and wherein Ar is selected from the group consisting of aryl and heteroaryl.

13. A process for producing a substituted phenol which comprises:
   (a) reacting in a reaction vessel an arene with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to produce an arylboronic ester; and
   (b) oxidizing the arylboronic ester formed in the reaction vessel with a hydrogenating oxidizing compound to produce the substituted phenol.

14. The process of claim 13 wherein the oxidizing compound is a peroxy compound selected from the group consisting of peroxymonosulfuric acid and salts thereof.

15. The process of claim 13 wherein the oxidizing compound is an organic peroxide.

16. The process of claim 13 wherein the oxidizing compound is hydrogen peroxide.

17. The process of claim 13 wherein the oxidizing compound is an alkali metal peroxymonosulfate.

18. The process of claim 15 wherein the alkali metal peroxymonosulfate is potassium peroxymonosulfate.

19. The process of claim 13 wherein the oxidizing compound is $2KHSO_5 \cdot KHSO_4 \cdot K_2SO_4$.

20. The process of claim 13 wherein the iridium complex is selected from the group consisting of $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B))_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

21. The process of claim 13 wherein the iridium complex is $(Ind)Ir(COD)$ wherein Ind is indenyl and COD is 1,5-cyclooctadiene.

22. The process of claim 13 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

23. The process of claim 13 wherein the borane is pinacolborane (BPin).

24. The process of claim 13 wherein the substituted phenol has the general formula RR'R"Ar(OH) wherein R, R', and R" are each independently selected from the group consisting of hydrogen, halo, alkyl, alkoxy, carboxylic ester, amine, and amide and wherein Ar is selected from the group consisting of aryl and heteroaryl.

* * * * *

UNITED STATES PATENT AND TRADEMARK OFFICE
CERTIFICATE OF CORRECTION

PATENT NO. : 6,828,466 B2  
DATED : December 7, 2004  
INVENTOR(S) : Robert E. Maleczka, Jr. et al.

It is certified that error appears in the above-identified patent and that said Letters Patent is hereby corrected as shown below:

Column 10,
Line 8, "$R_{15}$, and $R1_6$" should be -- $R_{15}$, and $R_{16}$ --.

Column 33,
Line 58, "(d, T=239 Hz)," should be -- (d, J=239 Hz), --.

Column 35,
Line 20, "Chem. Tnt. Ed." should be -- Chem. Int. Ed. --.

Signed and Sealed this

Nineteenth Day of April, 2005

JON W. DUDAS  
*Director of the United States Patent and Trademark Office*